US012680129B2

(12) United States Patent
Kunihiro

(10) Patent No.: US 12,680,129 B2
(45) Date of Patent: Jul. 14, 2026

(54) SAMPLE PRESERVATION SOLUTION, AND ANALYSIS DEVICE AND ANALYSIS METHOD USING THE SAME

(71) Applicant: TECHNOSURUGA LABORATORY CO., LTD., Shizuoka (JP)

(72) Inventor: Tadao Kunihiro, Shizuoka (JP)

(73) Assignee: TECHNOSURUGA LABORATORY CO., LTD., Shizuoka (JP)

( * ) Notice: Subject to any disclaimer, the term of this patent is extended or adjusted under 35 U.S.C. 154(b) by 1168 days.

(21) Appl. No.: 17/640,410

(22) PCT Filed: Aug. 20, 2020

(86) PCT No.: PCT/JP2020/031367
§ 371 (c)(1),
(2) Date: Mar. 4, 2022

(87) PCT Pub. No.: WO2021/054028
PCT Pub. Date: Mar. 25, 2021

(65) Prior Publication Data
US 2022/0333156 A1      Oct. 20, 2022

(30) Foreign Application Priority Data
Sep. 18, 2019    (JP) ................................. 2019-169216

(51) Int. Cl.
| | |
|---|---|
| *C12Q 1/68* | (2018.01) |
| *A01N 1/12* | (2025.01) |
| *C12Q 1/02* | (2006.01) |
| *C12Q 1/686* | (2018.01) |

(52) U.S. Cl.
CPC .............. *C12Q 1/686* (2013.01); *A01N 1/12* (2025.01); *C12Q 1/02* (2013.01)

(58) Field of Classification Search
None
See application file for complete search history.

(56) References Cited

U.S. PATENT DOCUMENTS

| | | | |
|---|---|---|---|
| 5,601,993 A | 2/1997 | Kano et al. | |
| 2015/0010691 A1* | 1/2015 | Siddoway .............. | A23B 2/754 |
| | | | 426/654 |
| 2016/0333339 A1 | 11/2016 | Fischer et al. | |
| 2018/0201977 A1 | 7/2018 | Gaeta | |
| 2022/0333156 A1* | 10/2022 | Kunihiro .................. | A01N 1/12 |

FOREIGN PATENT DOCUMENTS

| | | | | | | |
|---|---|---|---|---|---|---|
| CN | 103827317 | A | * | 5/2014 | ........... | C12Q 1/6809 |
| CN | 107227306 | A | * | 10/2017 | ......... | C12N 15/1003 |
| CN | 108893523 | A | * | 11/2018 | .......... | C12Q 1/6806 |
| CN | 109122667 | A | * | 1/2019 | ............. | A01N 1/126 |
| JP | 6-180319 | A | | 6/1994 | | |
| JP | 2000-193660 | A | | 7/2000 | | |
| JP | 2016136911 | A | * | 8/2016 | | |
| WO | WO-2018138913 | A1 | * | 8/2018 | ............... | C12Q 1/02 |
| WO | WO-2021054028 | A1 | * | 3/2021 | ............... | C12Q 1/02 |

OTHER PUBLICATIONS

CN108893523A_Description, English Translation of CN108893523, pp. 1-6, pub Nov. 27, 2018 by Xiao Chuanxing (Year: 2018).*
JP2016136911A_Description, English Translation of JP2016136911A, pp. 1-5, pub. Aug. 4, 2016 by Hisada Takayoshi (Year: 2016).*
Nagashima et al., 2010. Effect of a *Lactobacillus* species on incidence of diarrhea in calves and change of the microflora associated with growth. Bioscience and microflora, 29(2), pp. 97-110. (Year: 2010).*
WO2018138913A1_Description is English Translation of WO2018-138913A1 filed Jan. 30, 2017, Pub Aug. 2, 2018 (Year: 2017).*
CN-107227306A_Description is English Translation of CN107227306A, filed Jun. 26, 2017, pub Oct. 3, 2017. (Year: 2017).*
CN-109122667A_Description is English Translation of CN 109122667A, filed Sep. 27, 2018, pub Jan. 4, 2019. (Year: 2019).*
CN103827317_Description is the English Translation of CN103827317A, pub May 28, 2017 (Year: 2017).*
Office Action dated Dec. 27, 2023, issued in counterpart CN Application No. 202080049100.7. (10 pages).
Extended (Supplementary)European Search Report dated Jul. 21, 2023, issued in counterpart EP Application No. 20864841.0. (7 pages).
Nagashima et al., "Effect of a *Lactobacillus* Species on Incidence of Diarrhea in Calves and Change of the Microflora Associated with Growth", Bioscience Microflora, 2010, vol. 29, No. 2, pp. 97-110, cited in Specification (14 pages).
International Search Report dated Nov. 17, 2020, issued in counterpart International Application No. PCT/JP2020/031367 (2 pages).

* cited by examiner

*Primary Examiner* — Gary Benzion
*Assistant Examiner* — Olayinka A Oyemyemi
(74) *Attorney, Agent, or Firm* — WHDA, LLP

(57) ABSTRACT

The present invention provides means with which bile acids, phenols, indoles and organic acids contained in a sample can be stably preserved without cryopreservation of the sample. A sample preservation solution of the present invention is a sample preservation solution used for analyzing at least one component selected from the group consisting of bile acids, phenols, indoles and organic acids contained in a biological or environmental sample, containing at least the following (A) and (B): (A) condensed phosphate or polyoxyethylene sorbitan alkylate; and (B) guanidinium thiocyanate, Tris-HCl (pH 7 to 9), and EDTA.

4 Claims, 11 Drawing Sheets
Specification includes a Sequence Listing.

Fig. 2(A)
Fig. 2(B)
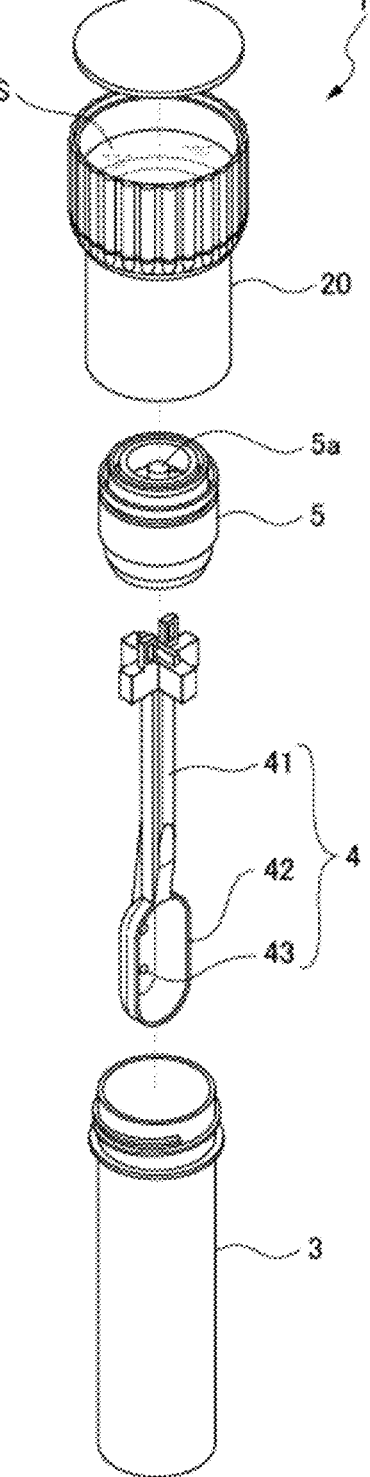
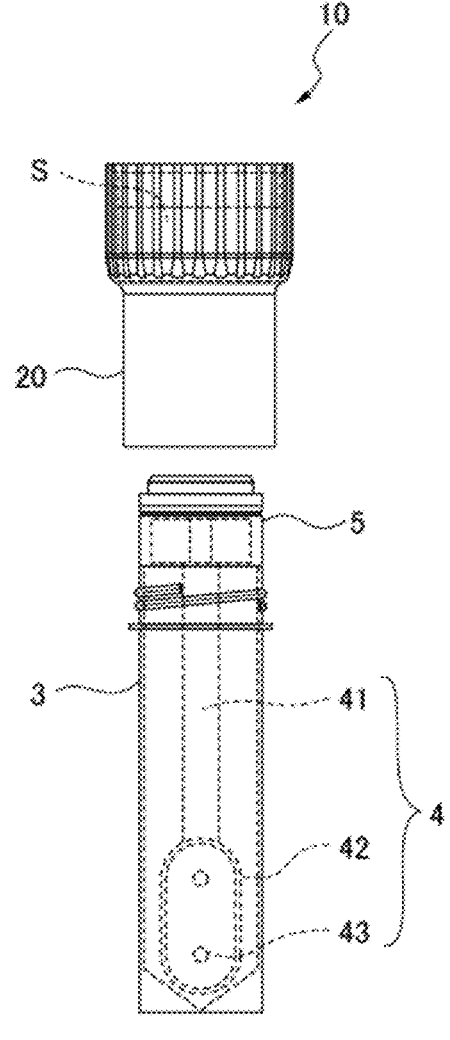

SAMPLE PRESERVATION SOLUTION, AND ANALYSIS DEVICE AND ANALYSIS METHOD USING THE SAME

TECHNICAL FIELD

The present invention relates to a sample preservation solution in which a component contained in a biological or environmental sample, such as bile acids, phenols, indoles and organic acids, can be stably preserved, and also relates to an analysis device including the sample preservation solution and an analysis method using the sample preservation solution.

BACKGROUND ART

In order to evaluate health conditions or medical conditions of a human or an animal, a biological sample such as feces is collected to analyze a microbial community structure present in the sample by a molecular biological method (Non Patent Literature 1). In addition to the analysis of a microbial community structure, metabolomic analysis for comprehensively elucidating metabolic activity in a living body by analyzing various metabolites contained in such a sample is recently performed in many cases.

A biological sample such as feces mainly contains organic substances and microbes, however, and hence is easily changed over time through decomposition of an organic substance by microbes, and growth, death and the like of the microbes, and is very unstable. Besides, a metabolite contained in the sample is also easily changed, for example, increased or decreased over time in the amount through oxidation, decomposition, volatilization and the like. Since the above-described analysis is performed in an inspection institute in which prescribed analytical instruments are installed, it is necessary to transport a collected sample to the inspection institute, and hence it takes time for the inspection institute to get the sample. Therefore, a problem is that an analyzed microbial community structure or an analysis value of a metabolite has been varied from that of the sample at the time of collection depending on time elapsed from the sample collection before performing the analysis, and a temperature, a storage method and the like employed during storage/transport.

Therefore, when the analysis of a microbial community structure and the analysis of a metabolite are to be performed, a sample is generally frozen for preservation immediately after collection for retaining contents of the sample at the time of the collection. Accordingly, it is actually impossible to collect a sample in a place having no refrigeration equipment, and even in a place having refrigeration equipment, it is sanitarily difficult to freeze a biological sample such as feces for preservation in ordinary home, workplace or the like. Besides, when analysis results of a sample obtained before and after a freezing treatment, and obtained before and after long-term freezing storage are examined, a detection ratio of some of microbial communities is deteriorated through the freezing treatment or the long-term freezing storage in some cases, and thus, there are problems that DNA degradation is suspected, and that an amount of an organic acid is changed.

Thus, as a method for stably preserving/transporting a sample without cryopreservation of the sample so as not to change a microbial community structure contained in the sample, the present applicant has reported, in Patent Literature 1, a method in which a sample is stored at normal temperature in a solution containing 0.01 M or more and less than 4 M guanidinium thiocyanate, 100 mM Tris-HCl (pH 9.0), and 40 mM EDTA. Also, the present applicant has proposed, in Patent Literature 2, a method for preserving a DNA and a chemical substance such as organic acids and polyamines of a sample by preserving, at room temperature, the sample in a solution containing any one or more of 4 M guanidinium thiocyanate, 100 mM Tris-HCl (pH 9.0) and 40 mM EDTA.

CITATION LIST

Patent Literature

Patent Literature 1
Japanese Patent Laid-Open No. 2016-136911
Patent Literature 2: International Publication No. WO2018/138913

Non Patent Literature

Non Patent Literature 1
Koji NAGASHIMA, Daisuke YASOKAWA, Kentaro ABE, Ryoji NAKAGAWA, Tooru KITAMURA, Toshiharu MIURA, Shu KOGAWA, Bioscience Microflora, Vol. 29, No. 2, 2010, p. 97-110

SUMMARY OF INVENTION

Technical Problem

In recent years, bile acids, decomposed substances (phenols and indoles) and organic acids contained in feces attract attention as metabolites that can be used for evaluating, from various aspects, an intestinal environment when analyzed together with analysis of intestinal flora. For example, a bile acid is a compound involved, in a living body, in cholesterol metabolism, digestion absorption of a fat-soluble component, and change of intestinal flora caused by surface activity. Bile acids are classified into primary bile acids biosynthesized in liver, and secondary bile acids generated through conversion of the primary bile acids with intestinal bacteria, and the secondary bile acids are toxic, and are said to be a promotor of carcinogenesis of colorectal cancer.

Phenols such as phenol, p-cresol and 4-ethylphenol are generated, in a living body, from tyrosine through the action of intestinal bacteria, and indoles such as indole and scatole are generated, in a living body, from tryptophan through the action of intestinal bacteria. These phenols and indoles are designated as decomposed substances, and are said to be a cause of a bad odor of feces and also known as an index of aggravation of intestinal environment. Many of the generated phenols harmfully affect epidermis formation process through blood, and hence are regarded as one of causes of a skin problem.

Furthermore, organic acids are compounds that work, in a living body, to keep the inside of the intestinal tract acidic and to accelerate intestinal peristalsis and water secretion from the intestinal tract, and have effects of infection protection, production inhibition of decomposed products, and improvement of defection/bowel movement. Organic acids are metabolites of dietary fiber and carbohydrate by intestinal bacteria, and are also increased through digestion of a protein or a peptide, and hence are regarded to be preferably evaluated together with intestinal flora.

Bile acids and metabolites such as phenols, indoles and organic acids contained in a feces sample are, however, easily increased/decreased in the amounts over time through oxidation, decomposition, volatilization and the like as described above, and hence, even when the sample is cryopreserved, the amounts of the metabolites are changed through a freezing treatment, long-term freezing storage and the like in some cases. Therefore, a problem is that the amounts of metabolites contained in a feces sample at the time of collection is difficult to analyze.

Patent Literature 1 and Patent Literature 2 describe preservation methods in which a sample can be stably preserved/transported without freezing, but in these literatures, no examination is made with attention paid to at least bile acids, phenols and indoles to stably preserve/transport these metabolites, and effectiveness is unknown.

Accordingly, the present invention was devised in consideration of the above-described points, and an object is to provide means with which bile acids, phenols, indoles and organic acids contained in a sample can be stably preserved without cryopreservation of the sample.

Another object of the present invention is to provide means with which bile acids and metabolites such as phenols, indoles and organic acids contained in a sample can be stably preserved and also a microbial community structure contained in the sample can be stably preserved.

Solution to Problem

In order to solve the above-described problems, a sample preservation solution of the present invention is a sample preservation solution used for analyzing at least one component selected from the group consisting of bile acids, phenols, indoles and organic acids contained in a biological or environmental sample, and contains at least the following (A) and (B): (A) condensed phosphate or polyoxyethylene sorbitan alkylate; and (B) guanidinium thiocyanate, Tris-HCl (pH 7 to 9), and EDTA.

When a sample is preserved in the sample preservation solution containing (A) condensed phosphate or polyoxyethylene sorbitan alkylate, and (B) guanidinium thiocyanate, Tris-HCl (pH 7 to 9) and EDTA, bile acids, phenols, indoles or organic acids contained in the sample can be stably preserved under a room temperature condition of 30° C. or less over at least 2 weeks. Besides, a microbial community structure contained in the sample can be stably preserved, and therefore, analysis of bile acids and metabolites such as phenols, indoles and organic acids and analysis of the microbial community structure can be performed based on samples preserved in the same sample preservation solution. Furthermore, since the compounding ingredients of the sample preservation solution of the present invention do not contain an interfering substance for performing the analysis of metabolites and the analysis of a microbial community structure, there is no need to perform a pretreatment, and operations for these analysis and the like can be performed in accordance with general protocols. It is noted that the term "room temperature" used herein refers to 1 to 30° C. (in conformity with The Japanese Pharmacopoeia). Besides, the term "being stably preserved" used herein refers to that a difference between analysis values obtained before and after a preservation period of samples is within 30%.

The condensed phosphate of the sample preservation solution of the present invention is preferably 5 mM to 150 mM sodium pyrophosphate. Thus, a preferable compound and its preferable concentration in the preservation solution as the condensed phosphate are selected.

The polyoxyethylene sorbitan alkylate of the sample preservation solution of the present invention is preferably 0.2 to 1.0% by weight polyoxyethylene sorbitan monolaurate. Thus, a preferable compound and its preferable concentration in the preservation solution as the polyoxyethylene sorbitan alkylate are selected.

Furthermore, it is preferable, in the sample preservation solution of the present invention, that the concentration of the guanidinium thiocyanate is 0.1 M to 5M, the concentration of Tris-HCl (pH 7 to 9) is 40 mM to 150 mM, and the concentration of EDTA is 1 mM to 50 mM. Thus, preferable concentrations of the respective ingredients are selected.

The sample applied to the sample preservation solution of the present invention is preferably feces. Thus, a preferable sample is selected.

An analysis device of the present invention includes a preservation container for preserving a sample, and the sample preservation solution described above, and is configured such that the sample is preserved in the preservation container in the state of being immersed or suspended in the sample preservation solution. Thus, the sample is preserved in the preservation container in the state of being immersed or suspended in the sample preservation solution, and therefore, anyone can easily perform procedures from collection of a sample to preservation/transport thereof, and analysis can be performed with the sample in the state of being stably preserved.

The analysis device of the present invention is preferably configured such that a volume ratio of an amount of the sample preservation solution to that of the sample is the sample:the sample preservation solution=1:3 or more. Thus, a preferable ratio, to be employed, of the amount of the sample preservation solution to that of the sample to be preserved is selected.

An analysis method of the present invention includes a step of adding the sample preservation solution described above to a sample and preserving the sample; and a step of analyzing at least one compound selected from the group consisting of bile acids, phenols, indoles and organic acids contained in the sample after preservation for at least 7 days. Thus, even after the preservation for at least 7 days, increase/decrease and change of bile acids and metabolites such as phenols, indoles and organic acids contained in the sample are suppressed, and hence the analysis can be performed with high accuracy.

Advantageous Effects of Invention

According to the present invention, a sample preservation solution having the following excellent effects, and an analysis device and an analysis method using the same can be provided.

(1) Bile acids, phenols, indoles or organic acids contained in a sample can be stably preserved under a room temperature condition of 30° C. or less over at least 2 weeks.

(2) Since a microbial community structure contained in the sample can be also stably preserved, the microbial community structure can be analyzed by a molecular biological method using the same sample preserved in the sample preservation solution.

(3) Since an interfering substance for performing analysis of a metabolite and analysis of a microbial community structure is not contained, there is no need to perform a pretreatment, and a sample can be applied to analysis through usual operations.

(4) When an analysis device including a preservation container for preserving a sample, and a sample preservation solution is used, the sample can be stably preserved and transported under a room temperature environment of 30° C. or less, and hence analysis of the sample can be easily performed. Besides, since the sample can be stably preserved for at least 2 weeks, the present invention is applicable to analysis of a sample transported a long distance.

BRIEF DESCRIPTION OF DRAWINGS

FIG. 2(A) is an exploded perspective view illustrating a second embodiment of the analysis device of the present invention, and FIG. 2(B) is a front view thereof.

DESCRIPTION OF EMBODIMENTS

Figure 1:
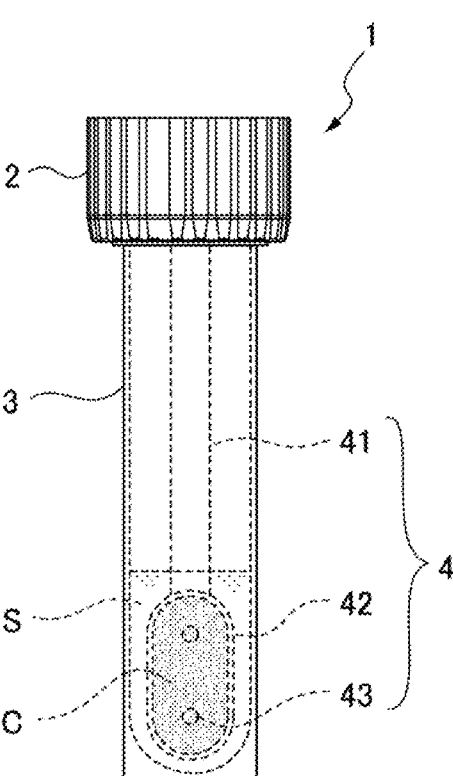
FIG. 1 is a front view illustrating a first embodiment of an analysis device of the present invention, and a use state thereof.

Hereinafter the present invention will be described in detail. A sample preservation solution of the present invention contains at least the following component (A) and component group (B), the component (A) is condensed phosphate or polyoxyethylene sorbitan alkylate, and the component group (B) includes guanidinium thiocyanate, Tris-HCl (pH 7 to 9), and EDTA. It is noted that a solvent of the sample preservation solution of the present invention is water.

The component (A) is condensed phosphate or polyoxy-ethylene sorbitan alkylate, and when the component (A) is blended in addition to the component group (B) described below, bile acids, phenols, indoles or organic acids can be stably preserved under a room temperature condition of 30° C. or less over at least 2 weeks. Therefore, such a component is regarded to have an action to prevent oxidation, decom-position, volatilization or the like of bile acids, phenols, indoles or organic acids in the sample preservation solution.

Examples of the condensed phosphate of the component (A) include pyrophosphate, metaphosphate, and polyphos-phate, and specific examples include sodium pyrophosphate, potassium pyrophosphate, sodium metaphosphate, potas-sium metaphosphate, sodium polyphosphate, and potassium polyphosphate. Among these, sodium pyrophosphate is suit-ably used from the viewpoint of an excellent effect of preserving bile acids, phenols, indoles and organic acids in the sample preservation solution. A concentration of the condensed phosphate blended in the sample preservation solution is preferably 1 mM to 300 mM, more preferably 5 mM to 150 mM, and particularly preferably 10 mM to 100 mM.

On the other hand, as the polyoxyethylene sorbitan alky-late of the component (A), one having water solubility is suitably used, and specific examples include polyoxyethylene sorbitan monolaurate (Tween 20), polyoxyethylene sorbitan monopalmate (Tween 40), polyoxyethylene sorbitan monostearate (Tween 60), and polyoxyethylene sorbitan monooleate (Tween 80). Among these, polyoxyethylene sorbitan monolaurate (Tween 20) is particularly suitably used from the viewpoint of an excellent effect of preserving bile acids, phenols, indoles or organic acids in the sample preservation solution. A concentration of the polyoxyethylene sorbitan alkylate blended in the sample preservation solution is preferably 0.05% by weight to 3.0% by weight, more preferably 0.1% by weight to 2.0% by weight, and particularly preferably 0.2% by weight to 1.0% by weight.

The component group (B) includes guanidinium thiocyanate, Tris-HCl (pH 7 to 9), and EDTA, and the component group (A) mainly has an action to suppress microbial growth and activities to prevent DNA resynthesis/decomposition by denaturing protein of microbial cell wall contained in a sample. Thus, a microbial community structure contained in the sample is retained to be stably preserved. Besides, since the microbial growth and activities are thus suppressed, the component group has an action to suppress production and consumption of metabolites by microbes.

A concentration of the guanidinium thiocyanate of the component group (B) blended in the sample preservation solution is preferably 0.01 M to 5 M, more preferably 0.1 M to 5 mM, and particularly preferably 0.5 M to 4 M. Besides, a concentration of the Tris-HCl blended in the sample preservation solution is preferably 10 mM to 300 mM, more preferably 40 mM to 150 mM, and particularly preferably 50 mM to 100 mM. The pH of the Tris-HCL is preferably in a range of 7 to 9, and pH of 7.5 to 8.5 is more preferred, and pH of 8.0 is particularly preferred. A concentration of the EDTA blended in the sample preservation solution is preferably 1 mM to 50 mM, more preferably 10 mM to 50 mM, and particularly preferably 30 mM to 50 mM.

The sample preservation solution of the present invention may contain another component in addition to the above-described components as long as the actions and effects of the present invention are not impaired. Examples of another component include a colorant, a perfume, a dispersant, and a moisturizer.

The sample preserved in the sample preservation solution of the present invention is a biological or environmental sample. Examples of the biological sample include feces, rectal swab, urine, nasal discharge, sputum, saliva, tissue, blood and serum. Among these, although feces contains a large amount of microbes and organic substances, it can be stably preserved in the sample preservation solution of the present invention. Examples of the environmental sample include environmental water from of rivers, lakes and marshes, seas and the like, soil, wastewater, and water and sludge of a biological treatment tank obtained in sewage treatment.

In the present invention, components that are inhibited from changing in the amounts and contents in a sample by preserving the sample in the sample preservation solution are bile acids, phenols, indoles and organic acids. These components will now be described in detail.

Bile acids are steroid compounds biosynthesized in a living body from cholesterol. Bile acids stably preserved in the sample preservation solution of the present invention include primary bile acids, secondary bile acids, reaction intermediates thereof, and conjugated bile acids bound to amino acids. Specific examples of bile acids are not especially limited and include cholic acid, chenodeoxycholic acid, deoxycholic acid, lithocholic acid, ursodeoxycholic acid, hyodeoxycholic acid, dehydrocholic acid, isodeoxycholic acid, glycocholic acid, glycochenodeoxycholic acid, glycodeoxycholic acid, glycolithocholic acid, glycoursodeoxycholic acid, taurocholic acid, taurochenodeoxycholic acid, taurodeoxycholic acid, taurolithocholic acid, taurourodeoxycholic acid, $\alpha$ muricholic acid, $\beta$ muricholic acid, $\omega$ muricholic acid, tauro-$\alpha$ muricholic acid, tauro-$\beta$ muricholic acid, 7-oxodeoxycholic acid, and 7-oxolithocholic acid.

Phenols stably preserved in the sample preservation solution of the present invention include phenols generated in a living body from tyrosine through the action of intestinal bacteria, and examples include, but are not limited to, phenol, p-cresol and 4-ethylphenol. Similarly, indoles stably preserved in the sample preservation solution of the present invention include indoles generated in a living body from tryptophan through the action of intestinal bacterial, and examples include, but are not limited to, indole and scatole.

Organic acids stably preserved in the sample preservation solution of the present invention mainly include short chain fatty acids generated in a living body through the action of intestinal bacteria, and widely include other carboxylic acids in addition to the short chain fatty acids. Examples include acetic acid, propionic acid, n-butyric acid, isobutyric acid, n-valeric acid, isovaleric acid, caproic acid, formic acid, succinic acid, and lactic acid.

The sample preservation solution of the present invention is used with a sample to be preserved immersed or suspended therein for preservation. Thus, a metabolite can be stably preserved under a room temperature environment of 30° C. or less over at least 2 weeks. A volume ratio of an amount of the sample preservation solution to be used is preferably the sample:the sample preservation solution=1:3 or more, more preferably the sample the sample preservation solution=1:4 or more, and particularly preferably the sample:the sample preservation solution=1:5 or more.

The sample preservation solution of the present invention can stably preserve a metabolite such as bile acids described above and also suppress change of a microbial community structure contained in the sample. Therefore, the sample preservation solution can be used in various molecular biological methods using a DNA, such as real time PCR analysis, metagenomic analysis using a next generation sequencer, microbial community structure analysis such as T-RFLP analysis and DGGE analysis, DNA nucleotide sequence analysis of a biological cultured cell strain, RAPD analysis that is a method of DNA polymorphism analysis for identifying a strain, and microsatellite analysis. In this manner, since the analysis of a metabolite and the analysis of a microbial community structure can be performed using the same sample preserved in the sample preservation solution, the sample can be preserved/transported easily and simply, and in addition, these analysis can be definitely performed on the same sample, and thus, comprehensive evaluations from various aspects can be performed.

A storage temperature for preserving a sample using the sample preservation solution of the present invention is under a room temperature environment of 1 to 30° C., but the sample preservation solution of the present invention can stably preserve a metabolite and a microbial community structure also in a temperature range of 10 to 30° C., a temperature range of 15 to 30° C., a temperature range of 20 to 30° C., or a temperature range of 25 to 30° C.

Now, referring to FIGS. 1 to 3, an analysis device including the sample preservation solution, and a preservation container for preserving a sample will be described in detail.

First, the analysis device 1 according to a first embodiment illustrated in FIG. 1 will be described. The analysis device 1 of the present embodiment includes a bottomed cylindrical preservation container 3 having an opening at one end, the sample preservation solution S of the present invention contained in the preservation container 3, a cover member 2 for sealing the opening of the preservation container 3, and a sample collecting member 4 used for collecting a sample. The sample collecting member 4 has a spoon-shaped collecting portion 42, at a tip thereof, formed so that a prescribed amount of a sample can be scooped and held therein, and an axial portion 41 extending toward the opposite end. The axial portion 41 is connected on a tip side thereof to a rear surface of the cover member 2, and is formed so that the sample collecting member 4 can be manipulated with the cover member 2 grasped. The collecting portion 42 of the sample collecting member 4 is provided with two holes 43 penetrating a bottom thereof. The holes 43 provided in the collecting portion 42 are provided so as to cause the sample preservation solution S to come into contact with a sample C held in the collecting portion 42 through the holes 43 in the preservation container 3, and to cause the sample preservation solution S to flow into the bottom of the collecting portion 42. Thus, the sample C held in the collecting portion 42 is moved away from the bottom of the collecting portion 42 into the sample preservation solution S, and the sample C is dispersed and suspended in the sample preservation solution S, and therefore, the sample C can be preserved in a state of being definitely in contact with the sample preservation solution S of the present invention. Although the two holes 43 are provided on the bottom of the collecting portion 42 in the present embodiment, the number thereof is not especially limited, and a structure having no holes 43 may be employed.

The sample preservation solution S is, in a state of being used as illustrated in FIG. 1, contained in the preservation container 3 up to a position for completely immersing the collecting portion 42 of the sample collecting member 4. The sample preservation solution S is contained in the preservation container 3 in an amount with a volume ratio of preferably the sample C:the sample preservation solution S=1:3 or more, more preferably the sample C:the sample preservation solution S=1:4 or more, and particularly preferably the sample C:the sample preservation solution S=1:5 or more. In the present embodiment, for example, the volume of the collecting portion 42 of the sample collecting member 4 is 1 mL, while 5 mL of the sample preservation solution S is contained.

The analysis device 1 of FIG. 1 is used as follows: First, the cover member 2 of the analysis device 1 is opened, and the sample collecting member 4 is manipulated with the cover member 2 grasped to take the sample C in the collecting portion 42. The resultant sample collecting member 4 is put in the preservation container 3, the collecting portion 42 holding the sample C is immersed in the sample preservation solution S in the preservation container 3, and the preservation container 3 is sealed with the cover member 2. Thus, the sample C is stored in the analysis device 1 in a state of being immersed and suspended in the sample preservation solution S. After the storage, the sample can be preserved and transported at room temperature together with the analysis device 1.

Next, an analysis device 10 according to a second embodiment illustrated in FIGS. 2(A) to 3 will be described. The analysis device 10 of the present embodiment includes a bottomed cylindrical preservation container 3 having an opening at one end, a cover member 20 for sealing the opening of the preservation container 3, the sample preservation solution S of the present invention contained in a containment space within the cover member 20, a pressing member 5 capable of communicating the containment space within the cover member 20 with the preservation container 3 to move the sample preservation solution S into the preservation container 3, and a sample collecting member 4 used for collecting a sample. The sample collecting member 4 has a spoon-shaped collecting portion 42, at a tip thereof, formed so that a prescribed amount of a sample can be scooped and held therein, and an axial portion 41 extending toward the opposite end. A tip side of the axial portion 41 is connected to the inside of the pressing member 5, and the sample collecting member 4 is formed to be able to be manipulated with the outer circumferential surface of the pressing member 5 grasped. Besides, the collecting portion 42 of the sample collecting member 4 is provided with two holes 43 penetrating a bottom thereof. The function and action of the holes 43 are the same as those described in the first embodiment above.

Furthermore, as illustrated in FIGS. 2(A) and 2(B), the pressing member 5 incorporated between the cover member 20 and the preservation container 3 is provided with a pressing pin Sa on a side opposing the cover member 20. On the other hand, a bottom of the containment space within the cover member 20 is provided with a thin portion (not shown) formed to be breakable when pressed by the pressing pin Sa, so that when the preservation container 3 is sealed with the cover member 20, the pressing pin 5a of the pressing member 5 is formed to press the bottom of the cover member 20 to break the bottom to cause the sample preservation solution S in the containment space to leak out through the broken portion. The sample preservation solution S leaked out from the containment space within the cover member 20 flows through a gap of the pressing member 5 into the preservation container 3. In this manner, since a structure in which the sample preservation solution S is not precedently contained in the preservation container 3 is employed, there may be no spill or loss of the sample preservation solution S by mistake in putting the sample collecting member 4 in or out of the preservation container 3, and hence, the collected sample C can be definitely preserved in a prescribed amount of the sample preservation solution S. In addition, since the amount of the sample preservation solution S can be thus made constant, a weight of the sample C preserved in the preservation container 3 can be accurately calculated by measuring the weight of the analysis device 10, and thus, a concentration of a metabolite to be analyzed can be more accurately obtained.

Figure 3:
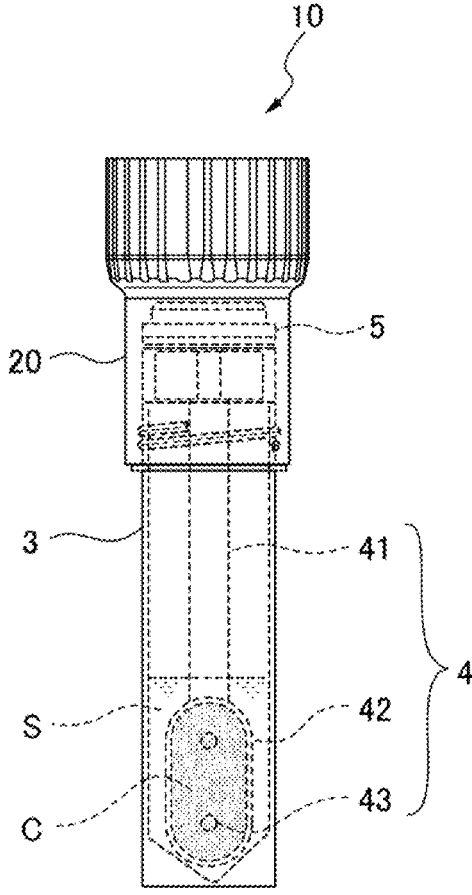
FIG. 3 is a front view illustrating a use state of the analysis device of the second embodiment of FIGS. 2(A) and 2(B).

The sample preservation solution S is, in a state of being used as illustrated in FIG. 3, contained in the containment space within the cover member 20 in an amount corresponding to a position for completely immersing the collecting portion 42 of the sample collecting member 4. The sample preservation solution S is contained in the cover member 20 in an amount with a volume ratio of preferably the sample C:the sample preservation solution S=1:3 or more, more preferably the sample C:the sample preservation solution S=1:4 or more, and particularly preferably the sample C:the sample preservation solution S=1:5 or more. In the present embodiment, for example, the volume of the collecting portion 42 of the sample collecting member 4 is 1 mL, while 5 mL of the sample preservation solution S is contained in the cover member 20.

The analysis device 10 of FIGS. 2(A) to 3 are used as follows: First, the cover member 20 of the analysis device 10 is opened, and the sample collecting member 4 is manipulated with the outer circumferential surface of the pressing member 5 grasped to take the sample C in the collecting portion 42. The resultant sample collecting member 4 is put in the preservation container 3 (with the sample preservation solution S not put in the preservation container 3 at this time point), and the pressing member 5 is fit toward the opening of the preservation container 3. Furthermore, the cover member 20 is caused to cover the pressing member 5, and the preservation container 3 is sealed with the cover member 20. At this point, since the pressing pin Sa of the pressing member 5 presses the bottom of the cover member 20, the bottom of the cover member 20 is broken, and the sample preservation solution S is leaked out through the bottom of the cover member 20 to flow through the pressing member 5 into the preservation container 3. In this manner, the collecting portion 42 holding the sample C is immersed in the sample preservation solution S within the preservation container 3, and the sample C is stored in a state of being immersed and suspended in the sample preservation solution S within the analysis device 10. After the storage, the sample can be preserved and transported at room temperature together with the analysis device 10.

Next, the present invention will be described in more detail with reference to examples; however, the present invention is not limited to these examples.

cyanate, 100 mM Tris-HCl, 40 mM EDTA (pH 8.0) and water; a "10 mM Na pyrophosphate/4 M GTC solution" containing 10 mM sodium pyrophosphate, 4 M guanidinium thiocyanate, 100 mM Tris-HCl, 40 mM EDTA (pH 8.0) and water; and a "4 M GTC solution" containing 4 M guanidinium thiocyanate, 100 mM Tris-HCl, 40 mM EDTA (pH 8.0) and water were used. In each of a sample suspension immediately before the storage at 30° C. (day 0) and a sample suspension after the storage (day 14), concentrations of phenol, p-cresol and 4-ethylphenol were measured by the following method. A prescribed amount of the sample suspension was precisely weighed in a centrifuge tube, and a phosphate buffer containing an internal standard substance (4-isopropylphenol) was added thereto to be mixed. The resultant was heated at 85° C. for 15 minutes, then cooled, and subjected to solvent extraction. The thus obtained crude extract solution was purified with a solid phase cartridge, and the resultant extract solution was used as a measurement specimen. The measurement specimen was used for measuring concentrations of phenol, p-cresol and 4-ethylphenol by a gas chromatography-mass spectrometry-selected ion monitoring method (GC-MS-SIM). Results are shown in Table 1 below and FIG. 4. It is noted that 4-ethylphenol was not detected in the feces sample B.

TABLE 1

| | Sample | Phenol (μg/g) | | p-Cresol (μg/g) | | 4-Ethylphenol (μg/g) | |
|---|---|---|---|---|---|---|---|
| | No. | day 0 | day 14 | day 0 | day 14 | day 0 | day 14 |
| 0.5% Tween20 4M GTC solution | A | 0.96 | 0.66 | 120.45 | 108.72 | 1.33 | 1.28 |
| | | 100% | 69% | 100% | 90% | 100% | 96% |
| | B | 45.48 | 40.62 | 60.96 | 57.42 | — | — |
| | | 100% | 89% | 100% | 94% | | |
| | C | 4.98 | 3.86 | 130.22 | 112.04 | 1.54 | 145 |
| | | 100% | 78% | 100% | 86% | 100% | 94% |
| 10 mM Na pyrophosphate 4M GTC solution | A | 0.96 | 0.77 | 120.45 | 113.03 | 1.33 | 0.95 |
| | | 100% | 81% | 100% | 94% | 160% | 72% |
| | B | 45.48 | 45.73 | 60.96 | 63.92 | — | — |
| | | 100% | 101% | 100% | 105% | | |
| | C | 4.98 | 4.12 | 130.22 | 113.23 | 1.54 | 1.57 |
| | | 100% | 69% | 100% | 90% | 100% | 96% |
| 4M GTC solution | A | 0.96 | 0.56 | 120.45 | 88.02 | 1.33 | 0.94 |
| | | 100% | 58% | 100% | 73% | 100% | 70% |
| | B | 45.48 | 37.41 | 60.96 | 50.32 | — | — |
| | | 100% | 82% | 100% | 83% | | |
| | C | 4.98 | 3.67 | 130.22 | 111.95 | 1.54 | 1.58 |
| | | 100% | 74% | 100% | 86% | 100% | 103% |

EXAMPLES

Example 1

1. Analysis (1) of Phenols Contained in Feces Sample

Figure 4:
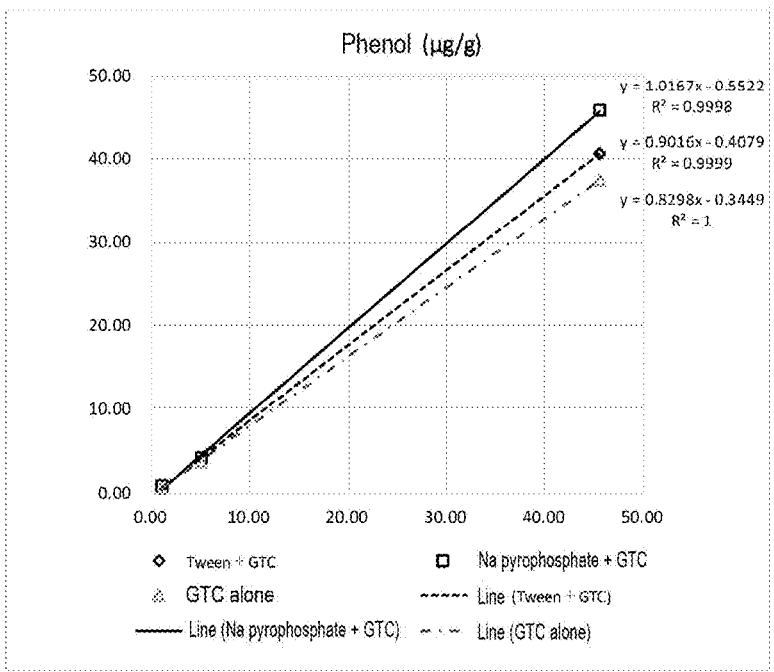
FIG. 4 is a graph illustrating a concentration of phenol contained in each sample suspension obtained before storage of a feces sample in each sample preservation solution (abscissa) and after the storage for 14 days (ordinate) in Example 1.

A feces sample cryopreserved in an ultra low temperature freezer at −80° C. immediately after collection was used, and feces samples A to C respectively obtained from 3 subjects were used. 1 g each of thawed feces samples was taken to be suspended in 5 mL of each of three sample preservation solutions, and the resultant was stored in a constant temperature bath at 30° C. for 14 days. As the three sample preservation solutions, a "0.5% Tween 20/4 M GTC solution" containing 0.5% by weight of Tween 20 (polyoxyethylene sorbitan monolaurate), 4 M guanidinium thio- In Table 1, a concentration of each substance to be measured is shown in an upper column, and a ratio (%) to a concentration before the storage (concentration on day 0) is shown in a lower column. It was revealed based on these results that phenol compounds in each feces sample can be stably retained after elapse of 14 days at 30° C. when the sample preservation solution in which Na pyrophosphate or Tween 20 is blended in addition to the 4 M GTC solution is used. Besides, FIG. 4 illustrates regression lines of the respective sample preservation solutions with the concentration of phenol in the feces sample before the storage (concentration on day 0) plotted on the abscissa, and with the concentration of phenol in the feces sample obtained on day 14 plotted on the ordinate. According to this graph, it was found that the sample preservation solution in which Na pyrophosphate or Tween 20 is blended in addition to the 4 M GTC solution has a larger slope of regression equation (close to 1), that even after the storage at 30° C. for 14 days, the concentrations of the phenols in the feces sample are not largely changed, and that the phenols can be thus quantitatively determined.

Example 2

2. Analysis (2) of Phenols Contained in Feces Sample

A feces sample cryopreserved in an ultra low temperature freezer at −80° C. immediately after collection was used, and this test was performed on a feces sample within 1 week after the cryopreservation at −80° C. Feces samples No. 1-1 to No. 1-6 obtained from 6 subjects were used. 1 g each of thawed feces samples was taken to be suspended in 5 mL of a sample preservation solution containing 100 mM sodium pyrophosphate, 4 M guanidinium thiocyanate, 100 mM Tris-HCl, 40 mM EDTA (pH 8.0) and water, and the resultant was stored in a constant temperature bath at 30° C. In each of a sample suspension immediately before the storage at 30° C. (day 0 raw feces) and sample suspensions after storage for 7 days (day 7), after storage for 14 days (day 14), and after storage for 28 days (day 28), concentrations of phenol, p-cresol and 4-ethylphenol were measured by a method similar to that of Example 1. A remaining portion of each feces sample was frozen at −80° C. again to be stored at −80° C. for 28 days, and then thawed to be suspended in the sample preservation solution in the same manner as described above. In this sample suspension (day 28 frozen feces), the concentrations of phenol, p-cresol and 4-ethylphenol were measured. Results of phenol are shown in Table 2 and FIG. 5, results of p-cresol are shown in Table 3 and FIG. 6, and results of 4-ethylphenol are shown in Table 4 and FIG. 7. It is noted that 4-ethylphenol was not detected in the feces samples No. 1-3, No. 1-5 and No. 1-6.

TABLE 2

| Phenol (µg/g) | Day 0 (raw feces) | Day 7 | Day 14 | Day 28 | Day 28 (frozen feces) |
|---|---|---|---|---|---|
| No. 1-1 | 5.00 | 5.31 | 4.04 | 5.23 | 4.44 |
| No. 1-2 | 11.01 | 11.69 | 8.21 | 10.33 | 11.24 |
| No. 1-3 | 7.65 | 9.17 | 6.31 | 7.49 | 8.13 |
| No. 1-4 | 7.30 | 5.23 | 5.45 | 5.01 | 6.92 |
| No. 1-5 | 1.76 | 1.53 | 2.03 | 1.78 | 1.37 |
| No. 1-6 | 11.43 | 7.86 | 9.80 | 7.01 | 8.74 |

TABLE 3

| p-Cresol (µg/g) | Day 0 (raw feces) | Day 7 | Day 14 | Day 28 | Day 28 (frozen feces) |
|---|---|---|---|---|---|
| No. 1-1 | 18.69 | 16.17 | 12.31 | 13.53 | 20.84 |
| No. 1-2 | 32.51 | 29.90 | 24.35 | 28.10 | 34.51 |
| No. 1-3 | 88.70 | 92.41 | 66.93 | 63.38 | 75.14 |
| No. 1-4 | 139.71 | 106.11 | 112.28 | 104.85 | 120.03 |
| No. 1-5 | 106.36 | 87.89 | 100.20 | 77.13 | 99.65 |
| No. 1-6 | 1.38 | 0.87 | 1.03 | 1.17 | 1.51 |

TABLE 4

| 4-Ethylphenol (µg/g) | Day 0 (raw feces) | Day 7 | Day 14 | Day 28 | Day 28 (frozen feces) |
|---|---|---|---|---|---|
| No. 1-1 | 20.93 | 18.62 | 16.23 | 16.63 | 16.92 |
| No. 1-2 | 0.48 | 0.45 | 0.41 | 0.50 | 0.48 |
| No. 1-4 | 6.37 | 4.77 | 4.62 | 4.84 | 6.96 |

Figure 5:
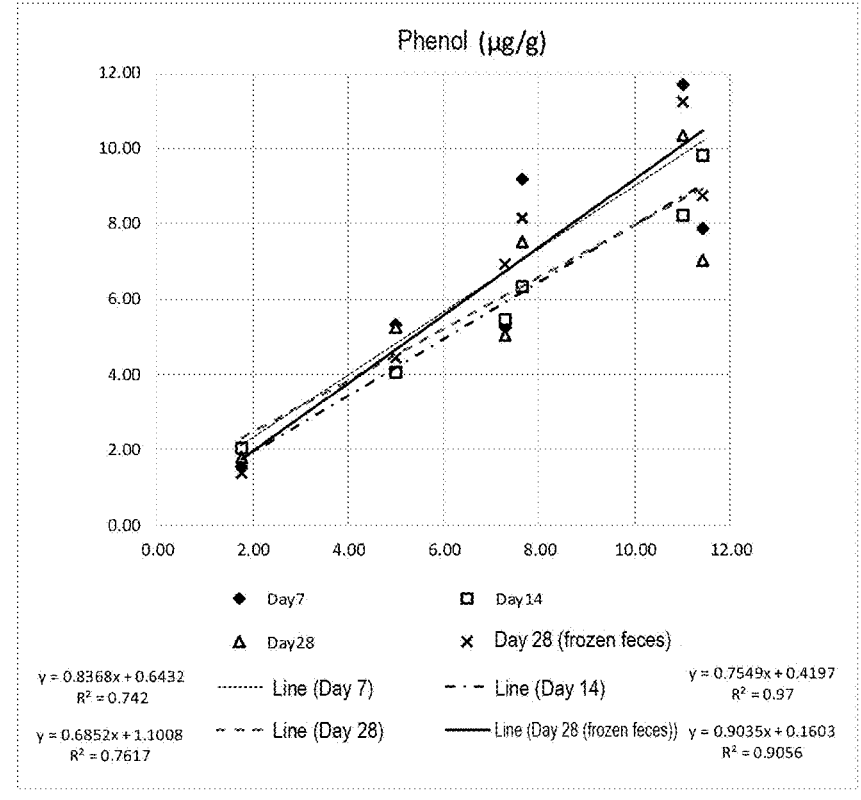
FIG. 5 is a graph illustrating a concentration of phenol contained in a sample suspension obtained before storage of a feces sample in a sample preservation solution (abscissa) and after the storage for a prescribed period (ordinate) in Example 2.
Figure 6:
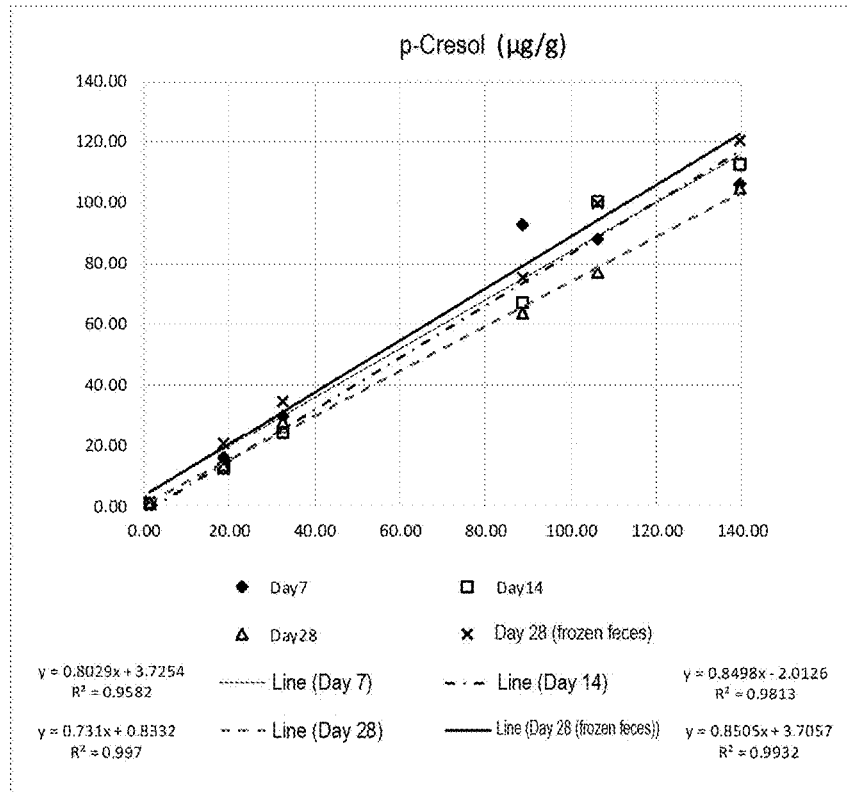
FIG. 6 is a graph illustrating a concentration of p-cresol contained in a sample suspension obtained before storage of a feces sample in a sample preservation solution (abscissa) and after the storage for a prescribed period (ordinate) in Example 2.
Figure 7:
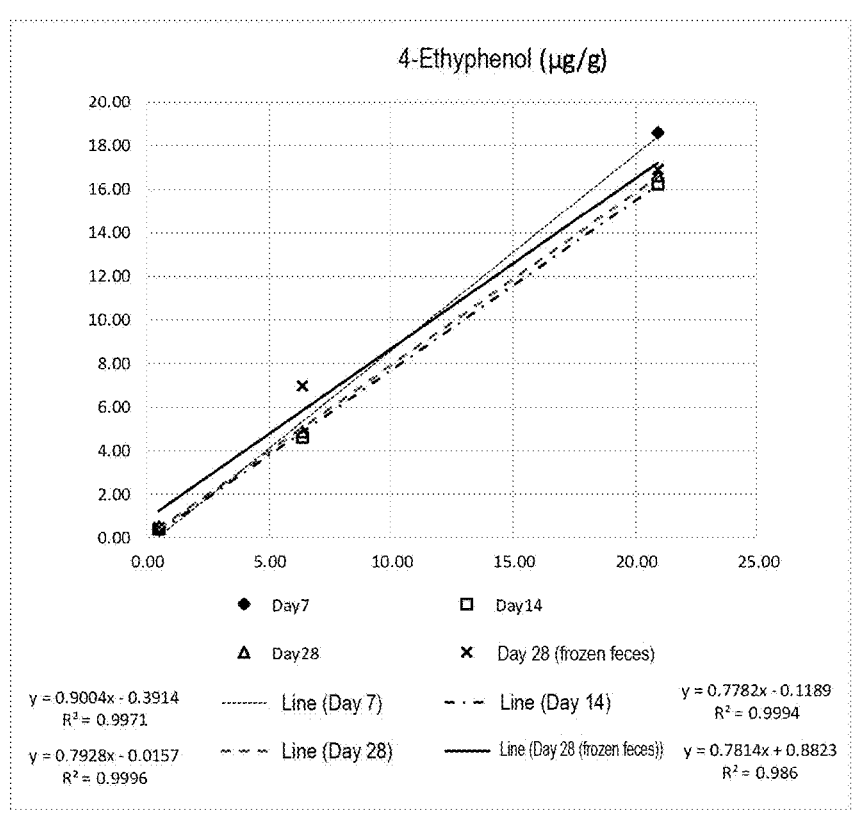
FIG. 7 is a graph illustrating a concentration of 4-eth-ylphenol contained in a sample suspension obtained before storage of a feces sample in a sample preservation solution (abscissa) and after the storage for a prescribed period (ordinate) in Example 2.

Tables 2 to 4 show the concentrations of each substance to be measured obtained at the respective measurement times. FIGS. 5 to 7 illustrate graphs of regression lines obtained based on these results with the concentration of each substance to be measured in the feces sample immediately before the storage at 30° C. (day 0 raw feces) plotted on the abscissa, and with the concentration of each substance to be measured in the feces sample obtained in each measurement time plotted on the ordinate. According to these graphs, the feces sample stored at 30° C. in the sample preservation solution of the present invention (100 mM sodium pyrophosphate+4 M GTC solution) was not largely changed in the concentrations as compared with the feces sample continuously stored at −80° C. for 28 days (day 28 (frozen feces)), and thus it was found that the feces sample can be stably stored at 30° C. for a long period of 28 days. Specifically, FIG. 5 reveals that similar analysis values are obtained for phenol through storage at 30° C. for 7 days (slope of regression equation: 0.84) and storage at −80° C. for 28 days (slope of regression equation: 0.90). It was also revealed that the analysis value tended to be slightly decreased through storage for 14 days or 28 days, but the slope of the regression equation remained at about 0.7. Besides, FIG. 6 reveals that similar analysis values were obtained for p-cresol through storage at 30° C. for 14 days (slope of regression equation: 0.80 to 0.85) and storage at −80° C. for 28 days (slope of regression equation: 0.85). It was also revealed that the analysis value tended to be slightly decreased through storage for 28 days, but the slope of the regression equation remained at about 0.7. Furthermore, FIG. 7 reveals that similar analysis values were obtained for 4-ethylphenol through storage at 30° C. for 28 days (slope of regression equation: 0.78 to 0.90) and storage at −80° C. for 28 days (slope of regression equation: 0.78).

Comparative Example 1

3. Analysis (3) of Phenols Contained in Feces Sample

A feces sample cryopreserved in an ultra low temperature freezer at −80° C. immediately after collection was used, and feces samples 1 to 3 respectively obtained from 3 subjects were used. 1 g each of thawed feces samples was taken to be suspended in 5 mL of each of four sample preservation solutions, and the resultant was stored in a constant temperature bath at 30° C. for 7 days. As the four sample preservation solutions, "20 mM Na pyrophosphate" containing 20 mM sodium pyrophosphate and water, "50 mM Na pyrophosphate" containing 50 mM sodium pyrophosphate and water, "100 mM Na pyrophosphate" containing 100 mM sodium pyrophosphate and water, and a "4 M GTC solution" containing 4 M guanidinium thiocyanate, 100 mM Tris-HCl, 40 mM EDTA (pH 8.0) and water were used. In each of a sample suspension immediately before the storage at 30° C. (day 0) and a sample suspension after the storage (day 7), concentrations of phenol, p-cresol and 4-ethylphenol were measured by a method similar to that of Example 1. Since 4-ethylphenol was not detected in the feces samples 1 to 3, measurement results of phenol and p-cresol are shown in Table 5 below.

TABLE 5

| | Sample | Phenol (μg/g) | | p-Cresol (μg/g) | |
|---|---|---|---|---|---|
| | No. | day 0 | day 7 | day 0 | day 7 |
| 20 mM | 1 | 0.85 | 6.30 | 38.67 | 467.87 |
| Na | | 100% | 741% | 100% | 1210% |
| pyrophosphate | 2 | 1.89 | 5.42 | 88.17 | 236.80 |
| | | 100% | 287% | 100% | 269% |
| | 3 | 0.33 | 22.18 | 78.93 | 233.68 |
| | | 100% | 6686% | 100% | 296% |
| 50 mM | 1 | 0.84 | 13.39 | 37.83 | 480.31 |
| Na | | 100% | 1586% | 100% | 1270% |
| pyrophosphate | 2 | 1.98 | 6.20 | 90.93 | 334.43 |
| | | 100% | 314% | 100% | 368% |
| | 3 | 0.42 | 71.55 | 66.83 | 296.47 |
| | | 100% | 16848% | 100% | 444% |
| 100 mM | 1 | 0.86 | 374.90 | 43.10 | 226.35 |
| Na | | 100% | 43609% | 100% | 525% |
| pyrophosphate | 2 | 2.10 | 7.93 | 97.50 | 344.91 |
| | | 100% | 377% | 100% | 354% |
| | 3 | 0.41 | 75.71 | 66.28 | 270.30 |
| | | 100% | 18384% | 100% | 408% |
| 4M | 1 | 2.72 | 1.88 | 44.18 | 41.63 |
| GTC | | 100% | 69% | 100% | 94% |
| solution | 2 | 5.05 | 2.12 | 103.12 | 85.34 |
| | | 100% | 42% | 100% | 83% |
| | 3 | 2.49 | 4.16 | 80.59 | 97.07 |
| | | 100% | 167% | 100% | 120% |

In Table 5, a concentration of each substance to be measured is shown in an upper column, and a ratio (%) to a concentration before the storage (concentration on day 0) is shown in a lower column. It was revealed based on these results that the phenol compounds in each feces sample were largely changed in the concentrations as compared with that before the storage when the sample preservation solution singly containing sodium pyrophosphate was used. As the concentration of sodium pyrophosphate blended was higher, the degree of the concentration change tended to be larger, and therefore, it was presumed that sodium pyrophosphate may possibly improve the growth of microbes contained in a feces sample. Examples 1 and 2 reveal, however, that a sample preservation solution capable of stably preserving phenols under a condition of 30° C. can be obtained by combining sodium pyrophosphate with the "4 M GTC solution" containing 4 M guanidinium thiocyanate, 100 mM Tris-HCl and 40 mM EDTA (pH 8.0).

Example 3

4. Analysis (1) of Bile Acids Contained in Feces Sample

Experimental Method

A feces sample cryopreserved in an ultra low temperature freezer at −80° C. immediately after collection was used, and feces samples A to D respectively obtained from 4 subjects were used. 1 g each of thawed feces samples was taken to be suspended in 5 mL of each of three sample preservation solutions, and the resultant was stored in a constant temperature bath at 30° C. for 14 days. As the three sample preservation solutions, the same solutions as those described in Example 1 were used. In each of a sample suspension immediately before the storage at 30° C. (day 0) and a sample suspension after the storage (day 14), concentrations of cholic acid, chenodeoxycholic acid and ursodeoxycholic acid were measured based on an analysis method of Kakiyama et al., (Kakiyama G, Muto A, Takei H, Nittono H, Murai T et al., A simple and accurate HPLC method for fecal bile acid profile in healthy and cirrhotic subjects: validation by GC-MS and LC-MS, J Lipid Res., 2014, Vol. 55, pp. 978-990). Incidentally, a pretreatment method for each specimen was modified as follows. A prescribed amount of the sample suspension was precisely weighed in a bead tube, and a 9-fold amount of a sodium acetate buffer/ethanol mixed solution was added thereto to pulverize the sample suspension. The resultant was heated at 85° C. for 30 minutes, cooled, and then centrifuged at 18,400×g for 10 minutes. The thus obtained supernatant was collected, diluted by 4 times with ultrapure water, and supplied to a solid phase extraction column (Bond Elut C18 cartridge, Agilent Technologies Japan, Ltd.) for solid phase extraction. The thus obtained extract was solidified by drying, the resultant was dissolved in 50% ethanol to be filtered through a hydrophilic PTFE filter having a hole size of 0.2 μm, and an internal standard solution was added to the resultant filtrate to obtain a measurement specimen solution. The concentrations of cholic acid, chenodeoxycholic acid and ursodeoxycholic acid in the measurement specimen solution were measured with a liquid chromatography-quadrupole time-of-flight mass spectrometer (LC-QTOF/MS). Results are shown in Table 6 below and FIGS. 8 and 9. It is noted that ursodeoxycholic acid was not detected in the feces samples A and C.

TABLE 6

| | Sample | Cholic acid (μmol/g) | | Chenodeoxycholic acid (μmol/g) | | Ursodeoxycholic acid (μmol/g) | |
|---|---|---|---|---|---|---|---|
| | No. | day 0 | day 14 | day 0 | day 14 | day 0 | day 14 |
| 0.5% Tween20 | A | 0.05 | 0.03 | 0.07 | 0.05 | — | — |
| 4M GTC solution | | 100% | 54% | 100% | 68% | | |
| | B | 5.03 | 4.37 | 2.90 | 2.54 | 0.93 | 0.79 |
| | | 100% | 87% | 100% | 88% | 100% | 85% |
| | C | 0.06 | 0.03 | 0.08 | 0.05 | — | — |
| | | 100% | 53% | 100% | 65% | | |
| | D | 0.84 | 0.66 | 0.45 | 0.39 | 0.64 | 0.55 |
| | | 100% | 79% | 100% | 86% | 100% | 85% |
| 10 mM Na | A | 0.05 | 0.03 | 0.07 | 0.05 | — | — |
| pyrophosphate | | 100% | 52% | 100% | 67% | | |
| 4M GTC solution | B | 5.03 | 4.84 | 2.90 | 2.88 | 0.93 | 0.67 |
| | | 100% | 96% | 100% | 99% | 100% | 94% |
| | C | 0.06 | 0.03 | 0.08 | 0.05 | — | — |
| | | 100% | 52% | 100% | 63% | | |
| | D | 0.84 | 0.73 | 0.45 | 0.43 | 0.64 | 0.57 |
| | | 100% | 87% | 100% | 84% | 100% | 89% |

TABLE 6-continued

| Sample No. | Cholic acid (μmol/g) day 0 | day 14 | Chenodeoxycholic acid (μmol/g) day 0 | day 14 | Ursodeoxycholic acid (μmol/g) day 0 | day 14 |
|---|---|---|---|---|---|---|
| 4M GTC solution A | 0.05 100% | 0.03 51% | 0.07 100% | 0.05 68% | — | — |
| B | 5.03 100% | 3.71 74% | 2.90 100% | 2.26 78% | 0.93 100% | 0.71 76% |
| C | 0.06 100% | 0.03 52% | 0.08 180% | 0.05 62% | — | — |
| D | 0.84 100% | 0.61 73% | 0.45 100% | 0.36 80% | 0.64 100% | 0.51 79% |

Figure 8:
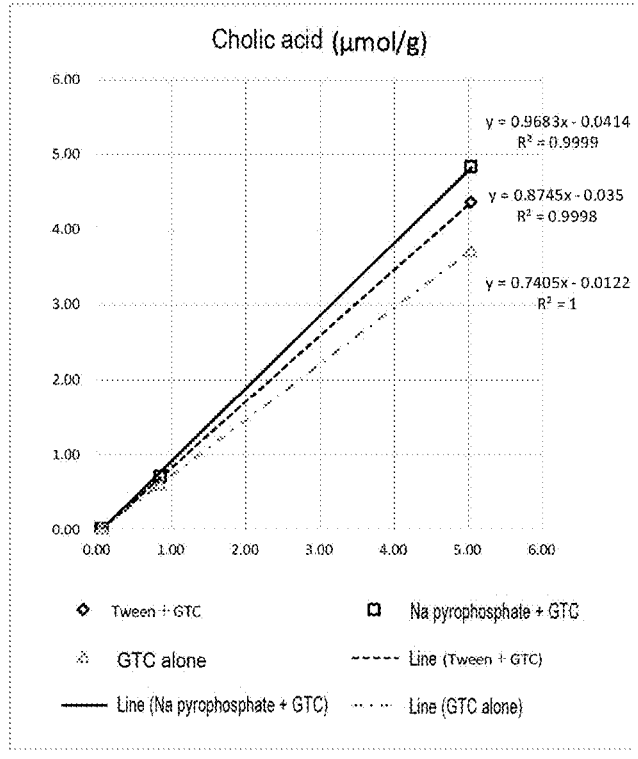
FIG. 8 is a graph illustrating a concentration of cholic acid contained in each sample suspension obtained before storage of a feces sample in each sample preservation solution (abscissa) and after the storage for 14 days (ordinate) in Example 3.
Figure 9:
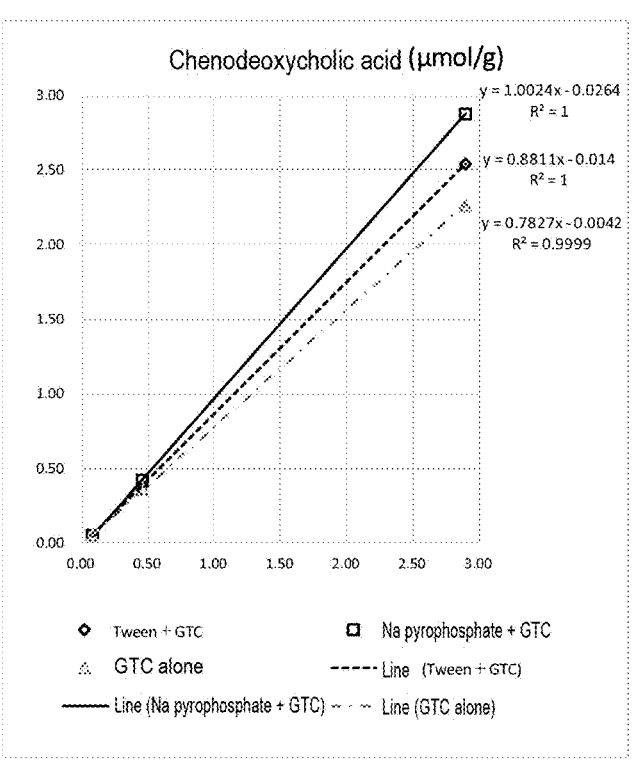
FIG. 9 is a graph illustrating a concentration of chenode-oxycholic acid contained in each sample suspension obtained before storage of a feces sample in each sample preservation solution (abscissa) and after the storage for 14 days (ordinate) in Example 3.

In Table 6, a concentration of each substance to be measured is shown in an upper column, and a ratio (%) to a concentration before the storage (concentration on day 0) is shown in a lower column. It was revealed based on these results that bile acid compounds such as cholic acid, chenodeoxycholic acid and ursodeoxycholic acid in the feces sample can be stably retained after elapse of 14 days at 30° C. when the sample preservation solution in which Na pyrophosphate or Tween 20 is blended in addition to a 4 M GTC solution is used. Besides, FIGS. 8 and 9 illustrate regression lines of the respective sample preservation solutions with the concentration of cholic acid or chenodeoxycholic acid in the feces sample before the storage (concentration on day 0) plotted on the abscissa, and with the concentration of cholic acid or chenodeoxycholic acid in the feces sample obtained on day 14 plotted on the ordinate. According to these graphs, it was found that the sample preservation solution in which Na pyrophosphate or Tween 20 is blended in addition to the 4 M GTC solution has a larger slope of regression equation (close to 1), that even after the storage at 30° C. for 14 days, the concentrations of the bile acids in the feces sample are not largely changed, and that the bile acids can be thus quantitatively determined.

Example 4

5. Analysis (2) of Bile Acids Contained in Feces Sample

A feces sample cryopreserved in an ultra low temperature freezer at −80° C. immediately after collection was used, and this test was performed on a feces sample within 1 week after the cryopreservation at −80° C. Feces samples No. 2-1 to No. 2-5 respectively obtained from different 5 subjects were used. 1 g each of thawed feces samples was taken to be suspended in 5 mL of a sample preservation solution containing 100 mM sodium pyrophosphate, 4 M guanidinium thiocyanate, 100 mM Tris-HCl, 40 mM EDTA (pH 8.0) and water, and the resultant was stored in a constant temperature bath at 30° C. In each of a sample suspension immediately before the storage at 30° C. (day 0 raw feces) and sample suspensions after storage for 7 days (day 7), after storage for 14 days (day 14), and after storage for 28 days (day 28), concentrations of cholic acid, chenodeoxycholic acid and ursodeoxycholic acid were measured by a method similar to that of Example 3. A remaining portion of each feces sample was frozen at −80° C. again to be stored at −80° C. for 28 days, and then thawed to be suspended in the sample preservation solution in the same manner as described above. In this sample suspension (day 28 frozen feces), the concentrations of cholic acid, chenodeoxycholic acid and ursodeoxycholic acid were measured. Results of cholic acid are shown in Table 7 and FIG. 10, results of chenodeoxycholic acid are shown in Table 8 and FIG. 11, and results of ursodeoxycholic acid are shown in Table 9 and FIG. 12. It is noted that ursodeoxycholic acid was not detected in the feces sample No. 2-5, and hence a feces sample No. 2-6 obtained from a different subject was used to perform a similar test.

TABLE 7

| Cholic acid (μmol/g) | Day 0 (raw feces) | Day 7 | Day 14 | Day 28 | Day 28 (frozen feces) |
|---|---|---|---|---|---|
| No. 2-1 | 0.70 | 0.57 | 0.64 | 0.59 | 0.64 |
| No. 2-2 | 2.07 | 2.06 | 2.04 | 1.71 | 2.01 |
| No. 2-3 | 1.90 | 1.89 | 1.79 | 1.62 | 1.74 |
| No. 2-4 | 0.51 | 0.41 | 0.38 | 0.42 | 0.46 |
| No. 2-5 | 0.11 | 0.10 | 0.18 | 0.15 | 0.10 |

TABLE 8

| Chenodeoxycholic acid (μmol/g) | Day 0 (raw feces) | Day 7 | Day 14 | Day 28 | Day 28 (frozen feces) |
|---|---|---|---|---|---|
| No. 2-1 | 0.53 | 0.45 | 0.52 | 0.42 | 0.55 |
| No. 2-2 | 0.88 | 0.67 | 0.76 | 0.56 | 0.81 |
| No. 2-3 | 0.92 | 0.70 | 0.71 | 0.58 | 0.70 |
| No. 2-4 | 0.41 | 0.38 | 0.41 | 0.32 | 0.38 |
| No. 2-5 | 0.11 | 0.15 | 0.16 | 0.14 | 0.10 |

TABLE 9

| Ursodeoxycholic acid (μmol/g) | Day 0 (raw feces) | Day 7 | Day 14 | Day 28 | Day 28 (frozen feces) |
|---|---|---|---|---|---|
| No. 2-1 | 0.18 | 0.15 | 0.16 | 0.19 | 0.14 |
| No. 2-2 | 1.18 | 1.05 | 1.07 | 0.82 | 1.07 |
| No. 2-3 | 0.28 | 0.26 | 0.25 | 0.25 | 0.23 |
| No. 2-4 | 0.32 | 0.32 | 0.31 | 0.28 | 0.29 |
| No. 2-6 | 0.19 | 0.19 | 0.16 | 0.19 | 0.17 |

Figure 10:
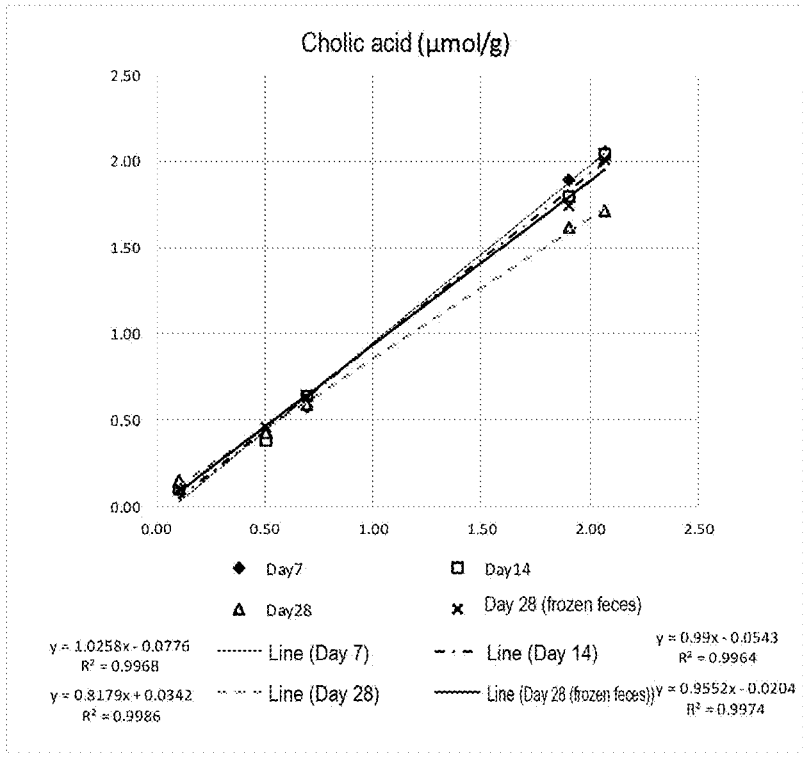
FIG. 10 is a graph illustrating a concentration of cholic acid contained in a sample suspension obtained before storage of a feces sample in a sample preservation solution (abscissa) and after the storage for a prescribed period (ordinate) in Example 4.
Figure 11:
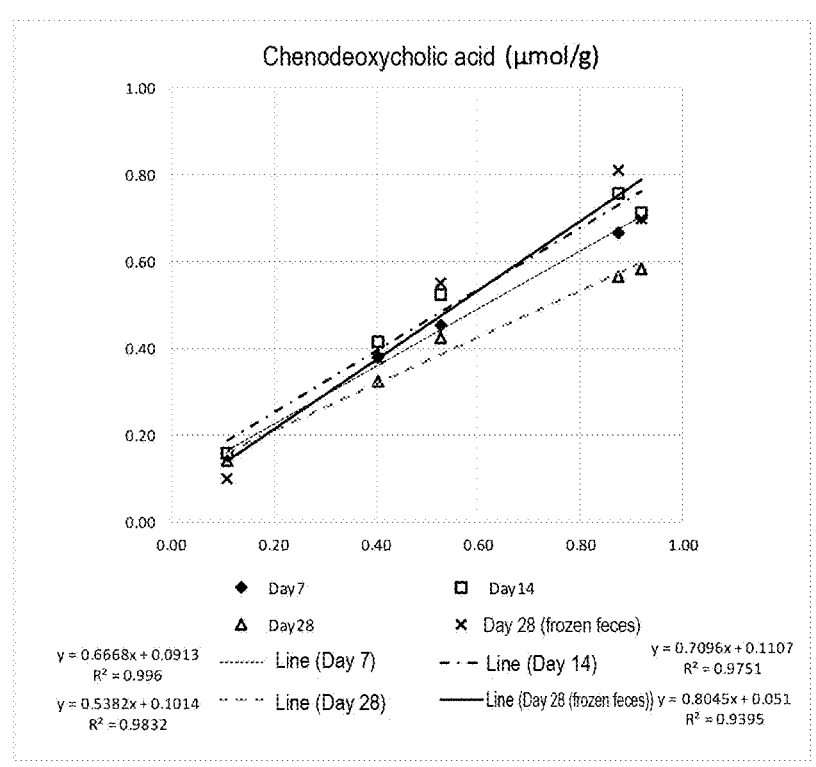
FIG. 11 is a graph illustrating a concentration of cheno-deoxycholic acid contained in a sample suspension obtained before storage of a feces sample in a sample preservation solution (abscissa) and after the storage for a prescribed period (ordinate) in Example 4.
Figure 12:
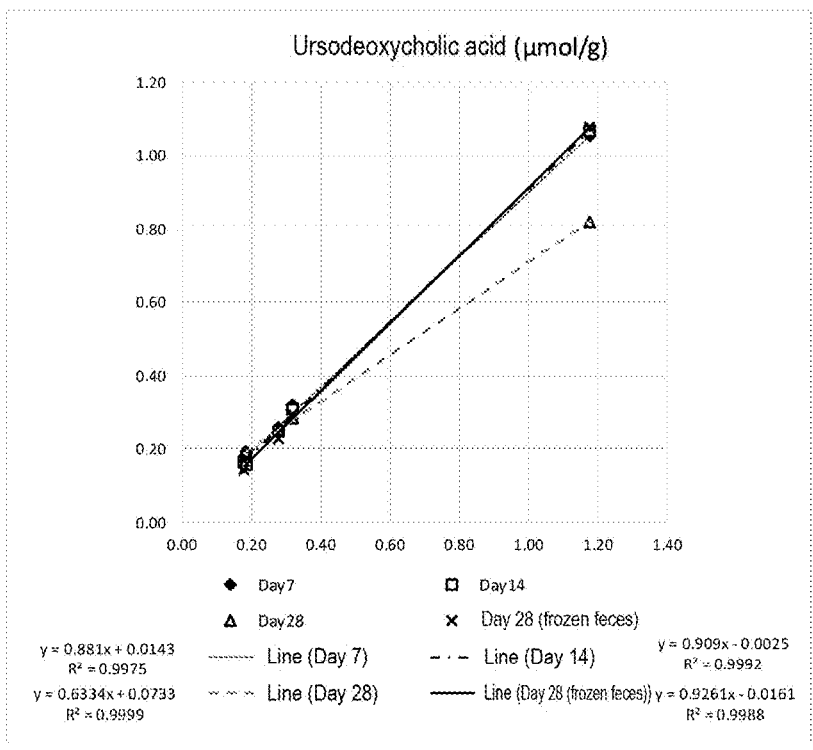
FIG. 12 is a graph illustrating a concentration of ursode-oxycholic acid contained in a sample suspension obtained before storage of a feces sample in a sample preservation solution (abscissa) and after the storage for a prescribed period (ordinate) in Example 4.

Tables 7 to 9 show the concentrations of each substance to be measured obtained at the respective measurement times. FIGS. 10 to 12 illustrate graphs of regression lines obtained based on these results with the concentration of each substance to be measured in the feces sample immediately before the storage at 30° C. (day 0 raw feces) plotted on the abscissa, and with the concentration of each substance to be measured in the feces sample obtained in each measurement time plotted on the ordinate. According to these graphs, the feces sample stored at 30° C. in the sample preservation solution of the present invention (100 mM sodium pyrophosphate+4 M GTC solution) was not largely changed in the concentrations as compared with the feces sample continuously stored at −80° C. for 28 days (day 28 (frozen feces)), and thus it was found that the feces sample can be stably stored at 30° C. for a long period of 28 days.

measurement specimen solution were measured with a high performance liquid chromatograph (product of Shimadzu Corporation, organic acid analysis system).

TABLE 10

| | Sample | Acetic acid (mg/g) | | Propionic acid (mg/g) | | n-Butyric acid (mg/g) | |
|---|---|---|---|---|---|---|---|
| | No. | day 0 | day 14 | day 0 | day 14 | day 0 | day 14 |
| 0.5% Tween20 | A | 1.00 | 1.06 | 0.52 | 0.50 | 0.34 | 0.33 |
| 4M GTC solution | | 100% | 108% | 100% | 96% | 100% | 98% |
| | B | 4.80 | 4.71 | 2.02 | 1.98 | 1.06 | 1.05 |
| | | 100% | 98% | 100% | 98% | 100% | 99% |
| | C | 1.37 | 1.29 | 0.99 | 0.90 | 1.81 | 1.64 |
| | | 100% | 94% | 100% | 91% | 100% | 91% |
| 10 mM Na | A | 1.00 | 1.14 | 0.52 | 0.47 | 0.34 | 0.31 |
| pyrophosphate | | 100% | 114% | 100% | 91% | 190% | 91% |
| 4M GTC solution | B | 4.80 | 5.06 | 2.02 | 2.10 | 1.06 | 1.10 |
| | | 100% | 106% | 100% | 104% | 100% | 104% |
| | C | 1.37 | 1.34 | 0.99 | 0.93 | 1.81 | 1.69 |
| | | 100% | 98% | 100% | 94% | 100% | 94% |
| 4M GTC solution | A | 1.00 | 1.19 | 0.52 | 0.53 | 0.34 | 0.36 |
| | | 100% | 119% | 100% | 103% | 100% | 108% |
| | B | 4.80 | 5.20 | 2.02 | 2.16 | 1.06 | 1.12 |
| | | 100% | 108% | 100% | 107% | 100% | 105% |
| | C | 1.37 | 1.27 | 0.99 | 0.89 | 1.81 | 1.62 |
| | | 100% | 93% | 100% | 91% | 100% | 90% |

Specifically, FIG. 10 reveals that similar analysis values were obtained for cholic acid through storage at 30° C. for 14 days (slope of regression equation: 0.99) and storage at −80° C. for 28 days (slope of regression equation: 0.96), and that the slope of the regression equation remained at 0.82 also through the storage at 30° C. for 28 days. Besides, FIG. 11 reveals that similar analysis values were obtained for chenodeoxycholic acid through storage at 30° C. for 14 days (slope of regression equation: 0.67 to 0.71) and storage at −80° C. for 28 days (slope of regression equation: 0.8). Furthermore, FIG. 12 reveals that similar analysis values were obtained for ursodeoxycholic acid through storage at 30° C. for 14 days (slope of regression equation: 0.88 to 0.91) and storage at −80° C. for 28 days (slope of regression equation: 0.93).

Example 5

6. Analysis (1) of Organic Acids Contained in Feces Sample

A feces sample cryopreserved in an ultra low temperature freezer at −80° C. immediately after collection was used, and feces samples A to C respectively obtained from 3 subjects were used. 1 g each of thawed feces samples was taken to be suspended in 5 mL of each of three sample preservation solutions, and the resultant was stored in a constant temperature bath at 30° C. for 14 days. As the three sample preservation solutions, the same solutions as those described in Example 1 were used. In each of a sample suspension immediately before the storage at 30° C. (day 0) and a sample suspension after the storage (day 14), concentrations of acetic acid, propionic acid and n-butyric acid were measured by the following method. A prescribed amount of the sample suspension was precisely weighed in a bead tube, and an extract solution was added thereto to be mixed. The resultant was heated at 85° C. for 15 minutes, and after cooling, the sample suspension was pulverized with beads and then centrifuged at 18,400×g for 10 minutes. The thus obtained supernatant was collected to be filtered through a membrane filter having a hole size of 0.20 µm to obtain a measurement specimen solution. The concentrations of acetic acid, propionic acid and n-butyric acid in the In Table 10, a concentration of each substance to be measured is shown in an upper column, and a ratio (%) to a concentration before the storage (concentration on day 0) is shown in a lower column. It was revealed based on these results that organic acid compounds in each feces sample can be stably retained after elapse of 14 days at 30° C. when the sample preservation solution in which Na pyrophosphate or Tween 20 is blended in addition to a 4 M GTC solution is used.

Example 6

7. Analysis (2) of Organic Acids Contained in Feces Sample

Figure 13:
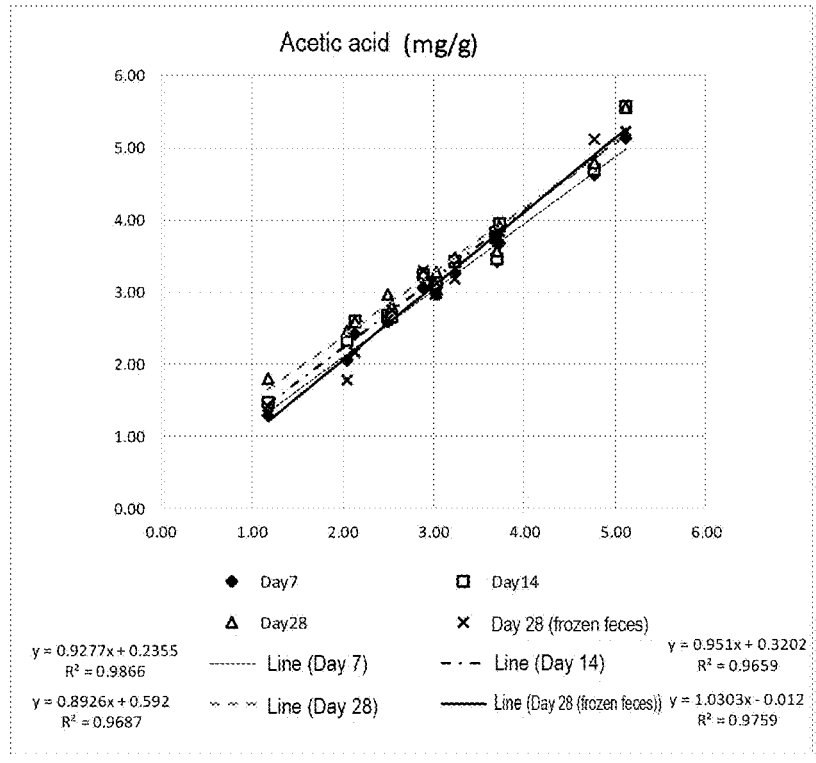
FIG. 13 is a graph illustrating a concentration of acetic acid contained in a sample suspension obtained before storage of a feces sample in a sample preservation solution (abscissa) and after the storage for a prescribed period (ordinate) in Example 6.
Figure 14:
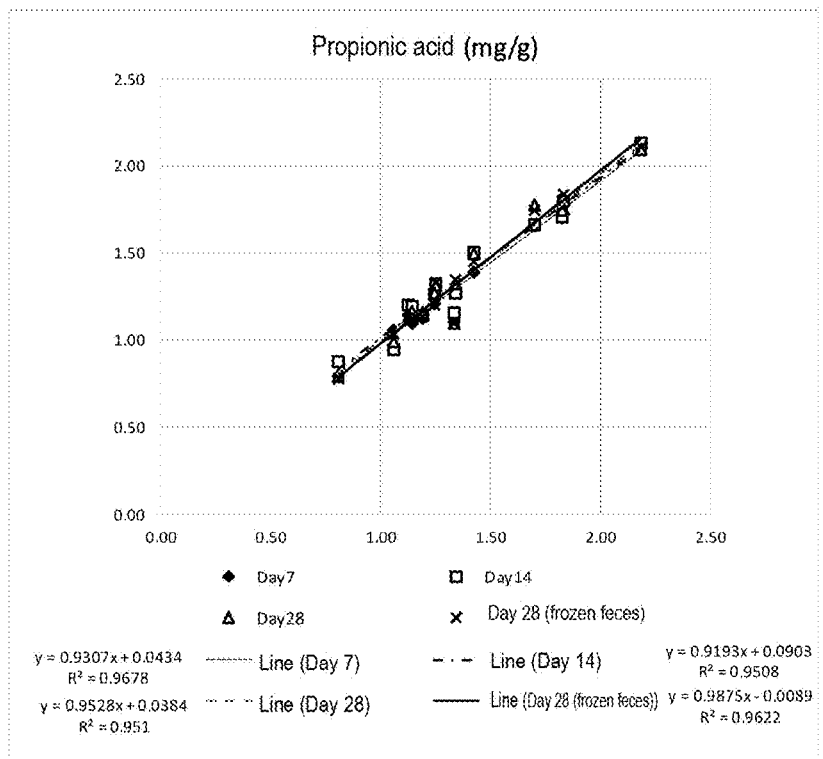
FIG. 14 is a graph illustrating a concentration of propionic acid contained in a sample suspension obtained before storage of a feces sample in a sample preservation solution (abscissa) and after the storage for a prescribed period (ordinate) in Example 6.
Figure 15:
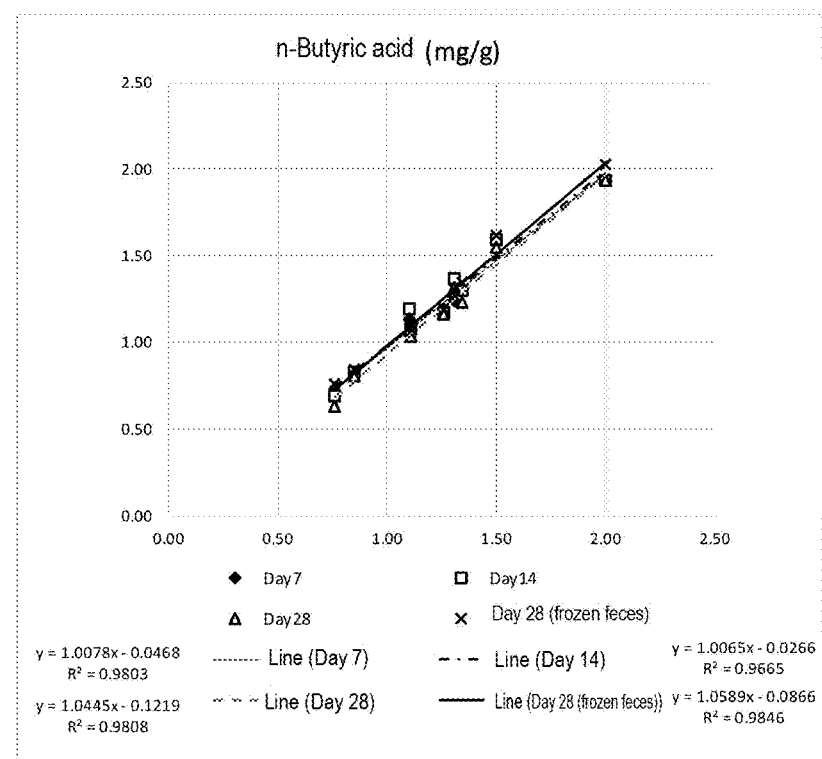
FIG. 15 is a graph illustrating a concentration of n-butyric acid contained in a sample suspension obtained before storage of a feces sample in a sample preservation solution (abscissa) and after the storage for a prescribed period (ordinate) in Example 6.

A feces sample cryopreserved in an ultra low temperature freezer at −80° C. immediately after collection was used, and this test was performed on a feces sample within 1 week after the cryopreservation at −80° C. Feces samples No. 3-1 to No. 3-14 respectively obtained from 14 subjects were used. 1 g each of thawed feces samples was taken to be suspended in 5 mL of a sample preservation solution containing 100 mM sodium pyrophosphate, 4 M guanidinium thiocyanate, 100 mM Tris-HCl, 40 mM EDTA (pH 8.0) and water, and the resultant was stored in a constant temperature bath at 30° C. In each of a sample suspension immediately before the storage at 30° C. (day 0 raw feces) and sample suspensions after storage for 7 days (day 7), after storage for 14 days (day 14), and after storage for 28 days (day 28), concentrations of acetic acid, propionic acid, n-butyric acid, n-valeric acid and iso-valeric acid were measured by HPLC in the same manner as in Example 5. A remaining portion of each feces sample was frozen at −80° C. again to be stored at −80° C. for 28 days, and then thawed to be suspended in the sample preservation solution in the same manner as described above. In this sample suspension (day 28 frozen feces), the concentrations of acetic acid, propionic acid, n-butyric acid, n-valeric acid and iso-valeric acid were measured. Results of acetic acid are shown in Table 11 and FIG. 13, results of propionic acid are shown in Table 12 and FIG. 14, results of n-butyric acid are shown in Table 13 and FIG. 15, and results of n-valeric acid are shown in Table 14 and FIG. 16, and results of iso-valeric acid are shown in Table 15 and FIG. 17. It is noted that n-butyric acid and n-valeric acid were not detected in the feces samples No. 3-10 to 3-14, and iso-valeric acid was not detected in the feces samples No. 3-3, 3-11, 3-13 and 3-14.

TABLE 11

| Acetic acid (mg/g) | Day 0 (raw feces) | Day 7 | Day 14 | Day 28 | Day 28 (frozen feces) |
|---|---|---|---|---|---|
| No. 3-1 | 2.14 | 2.41 | 2.60 | 2.57 | 2.16 |
| No. 3-2 | 3.03 | 3.01 | 3.09 | 3.10 | 2.96 |
| No. 3-3 | 4.78 | 4.63 | 4.69 | 4.78 | 5.12 |
| No. 3-4 | 3.69 | 3.68 | 3.82 | 3.83 | 3.76 |
| No. 3-5 | 2.90 | 3.06 | 3.23 | 3.25 | 3.30 |
| No. 3-6 | 2.51 | 2.57 | 2.67 | 2.95 | 2.82 |
| No. 3-7 | 3.71 | 3.43 | 3.45 | 3.56 | 3.76 |
| No. 3-8 | 3.73 | 3.67 | 3.94 | 3.91 | 3.83 |
| No. 3-9 | 3.04 | 2.97 | 3.12 | 3.27 | 2.97 |
| No. 3-10 | 2.54 | 2.66 | 2.65 | 2.79 | 2.74 |
| No. 3-11 | 2.05 | 2.04 | 2.32 | 2.44 | 1.78 |
| No. 3-12 | 1.18 | 1.29 | 1.46 | 1.79 | 1.40 |
| No. 3-13 | 3.24 | 3.25 | 3.41 | 3.47 | 3.18 |
| No. 3-14 | 5.12 | 5.13 | 5.57 | 5.55 | 5.22 |

TABLE 12

| Propionic acid (mg/g) | Day 0 (raw feces) | Day 7 | Day 14 | Day 28 | Day 28 (frozen feces) |
|---|---|---|---|---|---|
| No. 3-1 | 1.12 | 1.14 | 1.20 | 1.12 | 1.13 |
| No. 3-2 | 2.18 | 2.10 | 2.12 | 2.09 | 2.11 |
| No. 3-3 | 1.34 | 1.27 | 1.27 | 1.32 | 1.34 |
| No. 3-4 | 1.83 | 1.77 | 1.86 | 1.75 | 1.83 |
| No. 3-5 | 1.25 | 1.31 | 1.32 | 1.31 | 1.33 |
| No. 3-6 | 1.70 | 1.65 | 1.66 | 1.77 | 1.74 |
| No. 3-7 | 1.19 | 1.12 | 1.14 | 1.15 | 1.13 |
| No. 3-8 | 1.14 | 1.09 | 1.19 | 1.16 | 1.14 |
| No. 3-9 | 1.83 | 1.70 | 1.71 | 1.74 | 1.77 |
| No. 3-10 | 1.06 | 1.06 | 0.95 | 0.99 | 1.03 |
| No. 3-11 | 1.33 | 1.10 | 1.15 | 1.10 | 1.10 |
| No. 3-12 | 0.80 | 0.79 | 0.87 | 0.79 | 0.78 |
| No. 3-13 | 1.25 | 1.21 | 1.26 | 1.27 | 1.20 |
| No. 3-14 | 1.42 | 1.39 | 1.56 | 1.49 | 1.45 |

TABLE 13

| n-Butyric acid (mg/g) | Day 0 (raw feces) | Day 7 | Day 14 | Day 28 | Day 28 (frozen feces) |
|---|---|---|---|---|---|
| No. 3-1 | 1.11 | 1.12 | 1.18 | 1.07 | 1.07 |
| No. 3-2 | 1.12 | 1.06 | 1.07 | 1.03 | 1.05 |
| No. 3-3 | 2.00 | 1.94 | 1.93 | 1.93 | 2.02 |
| No. 3-4 | 1.35 | 1.29 | 1.23 | 1.22 | 1.33 |
| No. 3-5 | 1.50 | 1.58 | 1.59 | 1.54 | 1.61 |
| No. 3-6 | 0.85 | 0.81 | 0.82 | 0.80 | 0.83 |
| No. 3-7 | 1.25 | 1.19 | 1.16 | 1.16 | 1.18 |
| No. 3-8 | 1.32 | 1.23 | 1.36 | 1.30 | 1.30 |
| No. 3-9 | 0.76 | 0.70 | 0.69 | 0.63 | 0.75 |

TABLE 14

| n-Valeric acid (mg/g) | Day 0 (raw feces) | Day 7 | Day 14 | Day 28 | Day 28 (frozen feces) |
|---|---|---|---|---|---|
| No. 3-1 | 0.24 | 0.23 | 0.24 | 0.20 | 0.23 |
| No. 3-2 | 0.15 | 0.14 | 0.15 | 0.11 | 0.15 |
| No. 3-3 | 0.16 | 0.16 | 0.14 | 0.15 | 0.16 |
| No. 3-4 | 0.34 | 0.32 | 0.33 | 0.27 | 0.33 |

TABLE 14-continued

| n-Valeric acid (mg/g) | Day 0 (raw feces) | Day 7 | Day 14 | Day 28 | Day 28 (frozen feces) |
|---|---|---|---|---|---|
| No. 3-5 | 0.22 | 0.21 | 0.23 | 0.19 | 0.22 |
| No. 3-6 | 0.20 | 0.17 | 0.16 | 0.18 | 0.19 |
| No. 3-7 | 0.32 | 0.30 | 0.29 | 0.29 | 0.28 |
| No. 3-8 | 0.13 | 0.13 | 0.13 | 0.13 | 0.14 |
| No. 3-9 | 0.23 | 0.22 | 0.20 | 0.20 | 0.22 |

TABLE 15

| iso-Valeric acid (mg/g) | Day 0 (raw feces) | Day 7 | Day 14 | Day 28 | Day 28 (frozen feces) |
|---|---|---|---|---|---|
| No. 3-1 | 0.41 | 0.42 | 0.47 | 0.39 | 0.41 |
| No. 3-2 | 0.14 | 0.14 | 0.12 | 0.12 | 0.13 |
| No. 3-4 | 0.14 | 0.13 | 0.14 | 0.13 | 0.15 |
| No. 3-5 | 0.30 | 0.29 | 0.32 | 0.25 | 0.31 |
| No. 3-6 | 0.23 | 0.22 | 0.24 | 0.20 | 0.21 |
| No. 3-7 | 0.19 | 0.18 | 0.17 | 0.16 | 0.17 |
| No. 3-8 | 0.12 | 0.12 | 0.13 | 0.13 | 0.14 |
| No. 3-9 | 0.24 | 0.22 | 0.19 | 0.21 | 0.21 |
| No. 3-10 | 0.43 | 0.42 | 0.36 | 0.36 | 0.41 |
| No. 3-12 | 0.28 | 0.26 | 0.26 | 0.23 | 0.26 |

Figure 16:
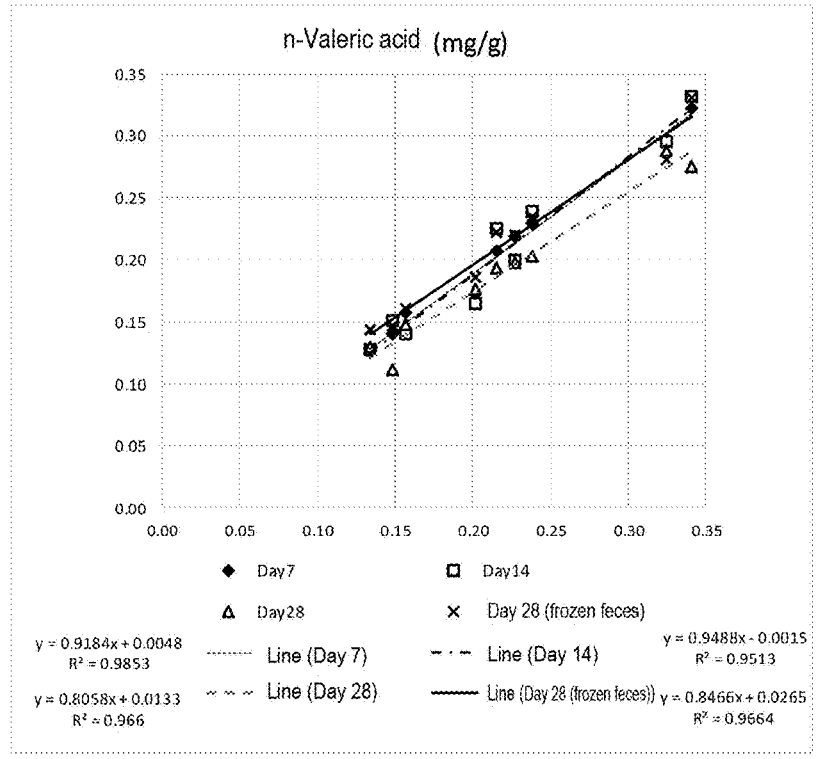
FIG. 16 is a graph illustrating a concentration of n-valeric acid contained in a sample suspension obtained before storage of a feces sample in a sample preservation solution (abscissa) and after the storage for a prescribed period (ordinate) in Example 6.
Figure 17:
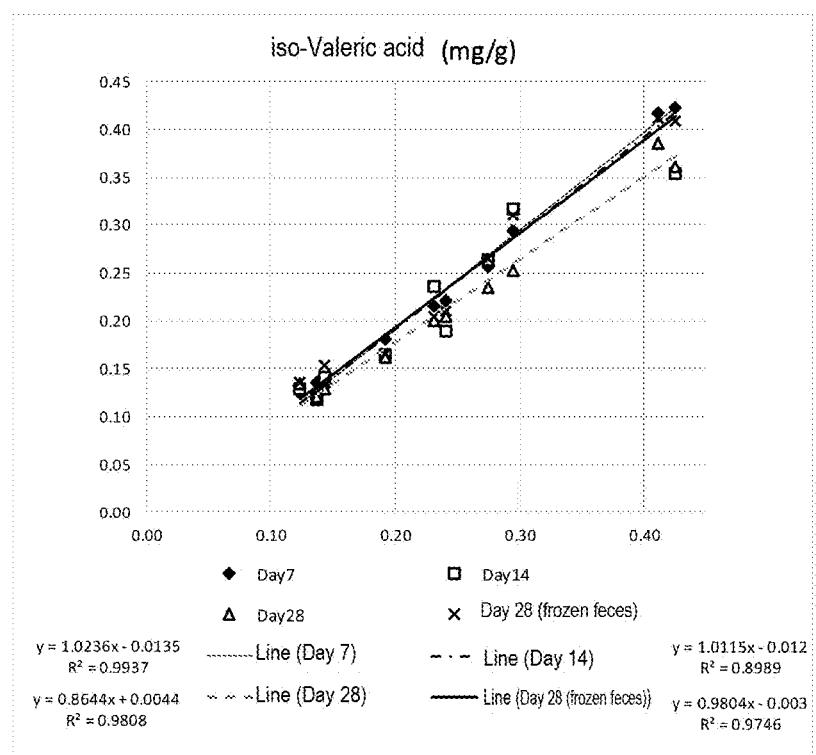
FIG. 17 is a graph illustrating a concentration of iso-valeric acid contained in a sample suspension obtained before storage of a feces sample in a sample preservation solution (abscissa) and after the storage for a prescribed period (ordinate) in Example 6.

Tables 11 to 15 show the concentrations of each substance to be measured obtained at the respective measurement times. FIGS. 13 to 17 illustrate graphs of regression lines obtained based on these results with the concentration of each substance to be measured in the feces sample immediately before the storage at 30° C. (day 0 raw feces) plotted on the abscissa, and with the concentration of each substance to be measured in the feces sample obtained in each measurement time plotted on the ordinate. According to these graphs, the feces sample stored at 30° C. in the sample preservation solution of the present invention (100 mM sodium pyrophosphate+4 M GTC solution) was not largely changed in the concentrations as compared with the feces sample continuously stored at −80° C. for 28 days (day 28 (frozen feces)), and thus it was found that the feces sample can be stably stored at 30° C. for a long period of 28 days. Specifically, FIG. 13 reveals that similar analysis values were obtained for acetic acid through storage at 30° C. for 28 days (slope of regression equation: 0.89 to 0.95) and storage at −80° C. for 28 days (slope of regression equation: 1.0). Besides, FIG. 14 reveals that similar analysis values were obtained for propionic acid through storage at 30° C. for 28 days (slope of regression equation: 0.92 to 0.95) and storage at −80° C. for 28 days (slope of regression equation: 0.99). Similarly, FIG. 15 reveals that similar analysis values were obtained for n-butyric acid through storage at 30° C. for 28 days (slope of regression equation: 1.00 to 1.04) and storage at −80° C. for 28 days (slope of regression equation: 1.06). FIG. 16 reveals that similar analysis values were obtained for n-valeric acid through storage at 30° C. for 28 days (slope of regression equation: 0.81 to 0.95) and storage at −80° C. for 28 days (slope of regression equation: 0.85). Furthermore, FIG. 17 reveals that similar analysis values were obtained for iso-valeric acid through storage at 30° C. for 14 days (slope of regression equation: 0.86 to 1.02) and storage at −80° C. for 28 days (slope of regression equation: 0.98).

Comparative Example 2                                          Example 7

8. Analysis (3) of Organic Acids Contained in Feces Sample

A feces sample cryopreserved in an ultra low temperature freezer at −80° C. immediately after collection was used, and feces samples 1 to 3 respectively obtained from 3 subjects were used. 1 g each of thawed feces samples was taken to be suspended in 5 mL of each of four sample preservation solutions, and the resultant was stored in a constant temperature bath at 30° C. for 7 days. As the four sample preservation solutions, "20 mM Na pyrophosphate" containing 20 mM sodium pyrophosphate and water, "50 mM Na pyrophosphate" containing 50 mM sodium pyrophosphate and water, "100 mM Na pyrophosphate" containing 100 mM sodium pyrophosphate and water, and a "4 M GTC solution" containing 4 M guanidinium thiocyanate, 100 mM Tris-HCl, 40 mM EDTA (pH 8.0) and water were used. In each of a sample suspension immediately before the storage at 30° C. (day 0) and a sample suspension after the storage (day 7), concentrations of acetic acid, propionic acid, n-butyric acid and iso-valeric acid were measured by a method similar to that of Example 5. Results are shown in Table 16 below.

9. Analysis (1) of Number of Microbes Contained in Feces Sample

A feces sample cryopreserved in an ultra low temperature freezer at −80° C. immediately after collection was used, and this test was performed on a feces sample within 1 week after the cryopreservation at −80° C. 19 feces samples obtained from different 19 subjects were used. 1 g each of thawed feces samples was taken to be suspended in 5 mL of a sample preservation solution containing 100 mM sodium pyrophosphate, 4 M guanidinium thiocyanate, 100 mM Tris-HCl, 40 mM EDTA (pH 8.0) and water, and the resultant was stored in a constant temperature bath at 30° C. From each of a sample suspension immediately before the storage at 30° C. (day 0 raw feces), and sample suspensions after storage for 14 days (day 14) and after storage for 28 days (day 28), a DNA was extracted. The extracted DNA was subjected to real time PCR to obtain the number of copies of a target gene (16S rRNA) of all eubacteria contained in 1 g of the specimen. A primer set for quantitatively determining the number of copies of all eubacteria used in the real time PCR had sequences of "341F: 5'-CCTACGG-

TABLE 16

| | Sample | Acetic acid (mg/g) | | Propionic acid (mg/g) | | n-Butyric acid (mg/g) | | iso-Valeric acid (mg/g) | |
|---|---|---|---|---|---|---|---|---|---|
| | No. | day 0 | day 7 | day 0 | day 7 | day 0 | day 7 | day 0 | day 7 |
| 20 mM | 1 | 4.06 | 16.92 | 1.89 | 4.70 | 1.36 | 12.03 | 0.16 | 1.76 |
| Na pyrophosphate | | 100% | 417% | 100% | 249% | 100% | 882% | 100% | 1093% |
| | 2 | 3.86 | 15.90 | 1.36 | 8.47 | 1.66 | 5.58 | 0.33 | 2.30 |
| | | 100% | 412% | 100% | 621% | 100% | 336% | 100% | 697% |
| | 3 | 1.47 | 10.39 | 0.77 | 3.78 | 0.35 | 2.81 | 0.26 | 0.78 |
| | | 100% | 707% | 100% | 493% | 100% | 806% | 100% | 295% |
| 50 mM | 1 | 4.10 | 19.42 | 1.91 | 5.29 | 1.38 | 12.97 | 0.17 | 2.43 |
| Na pyrophosphate | | 100% | 474% | 100% | 277% | 100% | 941% | 100% | 1425% |
| | 2 | 3.30 | 20.49 | 1.23 | 11.06 | 1.48 | 6.79 | 0.27 | 2.80 |
| | | 100% | 622% | 100% | 897% | 100% | 460% | 100% | 1032% |
| | 3 | 1.46 | 12.00 | 0.77 | 3.87 | 0.33 | 2.90 | 0.28 | 2.73 |
| | | 100% | 820% | 100% | 506% | 100% | 869% | 100% | 987% |
| 100 mM | 1 | 3.90 | 21.05 | 1.86 | 3.98 | 1.32 | 10.51 | 0.17 | 2.82 |
| Na pyrophosphate | | 100% | 540% | 100% | 214% | 100% | 797% | 100% | 1676% |
| | 2 | 3.47 | 20.26 | 1.35 | 10.14 | 1.59 | 5.72 | 0.30 | 3.06 |
| | | 100% | 584% | 100% | 751% | 100% | 360% | 100% | 1006% |
| | 3 | 1.53 | 10.68 | 0.74 | 3.34 | 0.32 | 3.14 | 0.28 | 0.58 |
| | | 100% | 698% | 100% | 453% | 100% | 989% | 100% | 208% |
| 4M GTC solution | 1 | 4.06 | 3.49 | 1.97 | 1.37 | 1.40 | 1.69 | 0.13 | 0.33 |
| | | 100% | 86% | 100% | 70% | 100% | 121% | 100% | 246% |
| | 2 | 3.21 | 3.92 | 1.26 | 1.90 | 1.56 | 1.35 | 0.26 | 0.14 |
| | | 100% | 122% | 100% | 151% | 100% | 87% | 100% | 54% |
| | 3 | 1.36 | 1.52 | 0.73 | 0.77 | 0.32 | 0.33 | 0.22 | 0.24 |
| | | 100% | 112% | 100% | 107% | 100% | 103% | 100% | 111% |

In Table 16, a concentration of each substance to be measured is shown in an upper column, and a ratio (%) to a concentration before the storage (concentration on day 0) is shown in a lower column. It was revealed based on these results that the organic acids in the feces sample were largely changed in the concentrations as compared with that before the storage when the sample preservation solution singly containing sodium pyrophosphate was used. Examples 5 and 6 reveal, however, that a sample preservation solution capable of stably preserving organic acids under a condition of 30° C. can be obtained by combining sodium pyrophosphate with the "4 M GTC solution" containing 4 M guanidinium thiocyanate, 100 mM Tris-HCl and 40 mM EDTA (pH 8.0).

GAGGCAGCAG-3'" and "534R: 5'-AT-TACCGCGGCTGCTGG-3'". The real time PCR was performed with a real time PCR machine (Rotor-Gene Q, product of Qiagen K. K.) and a real time PCR reagent (TB Green Premix Ex Taq II (Tli RNaseH Plus), product of Takara Bio Inc.). Results are illustrated in FIG. 18.

Figure 18:
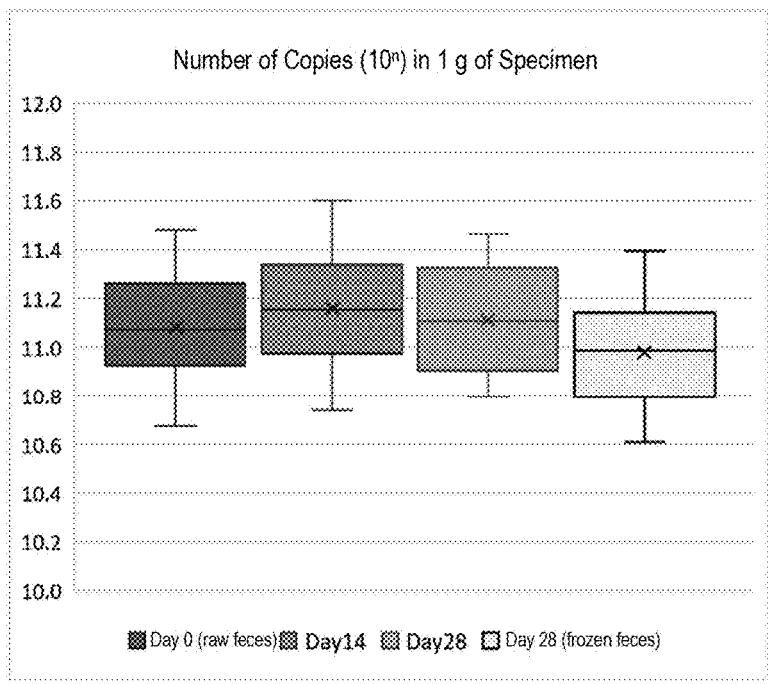
FIG. 18 is a graph illustrating results of real time PCR performed on DNAs extracted from sample suspensions obtained before storage of a feces sample in a sample preservation solution (day 0 raw feces and day 28 frozen feces) and after the storage for a prescribed period (day 14 and day 28) in Example 7.

In FIG. 18, the ordinate indicates the number of copies ($10^6$) of all eubacteria per g of the specimen. According to these graphs, the feces sample stored at 30° C. in the sample preservation solution of the present invention (100 mM sodium pyrophosphate+4 M GTC solution) was not largely changed in the number of copies as compared with the feces sample before the storage (day 0 (raw feces)), and thus it was found that the feces sample can be stably stored at 30° C. for a long period of 28 days. Incidentally, in a sample (day 28 (frozen feces)) obtained by freezing a remaining portion of each feces sample at −80° C. again to be stored at −80° C. for 28 days, and then thawing the resultant to be suspended in the sample preservation solution in the same manner as described above, the number of copies was slightly decreased.

Comparative Example 3

10. Analysis (2) of Number of Microbes Contained in Feces Sample

A feces sample cryopreserved in an ultra low temperature freezer at −80° C. immediately after collection was used, and feces samples respectively obtained from 5 subjects were used. 1 g each of thawed feces samples was taken to be suspended in 5 mL of each of four sample preservation solutions, and the resultant was stored in a constant temperature bath at 30° C. for 7 days. As the four sample preservation solutions, "20 mM Na pyrophosphate" containing 20 mM sodium pyrophosphate and water, "50 mM Na pyrophosphate" containing 50 mM sodium pyrophosphate and water, "100 mM Na pyrophosphate" containing 100 mM sodium pyrophosphate and water, and a "4 M GTC solution" containing 4 M guanidinium thiocyanate, 100 mM Tris-HCl, 40 mM EDTA (pH 8.0) and water were used. From each of a sample suspension immediately before the storage at 30° C. (day 0) and sample suspensions after the storage (storage day 3 and storage day 7), a DNA was extracted. The extracted DNA was subjected to real time PCR to measure the number of copies of a target gene (16S rRNA) of all eubacteria contained in 1 g of the specimen by a method similar to that of Example 7. Based on the thus obtained quantitative results, a change ratio on each date of storage was obtained with the sample suspension (day 0) immediately before the storage at 30° C. used as a reference (with a value of 1.0). Results are illustrated in FIG. 19.

Figure 19:
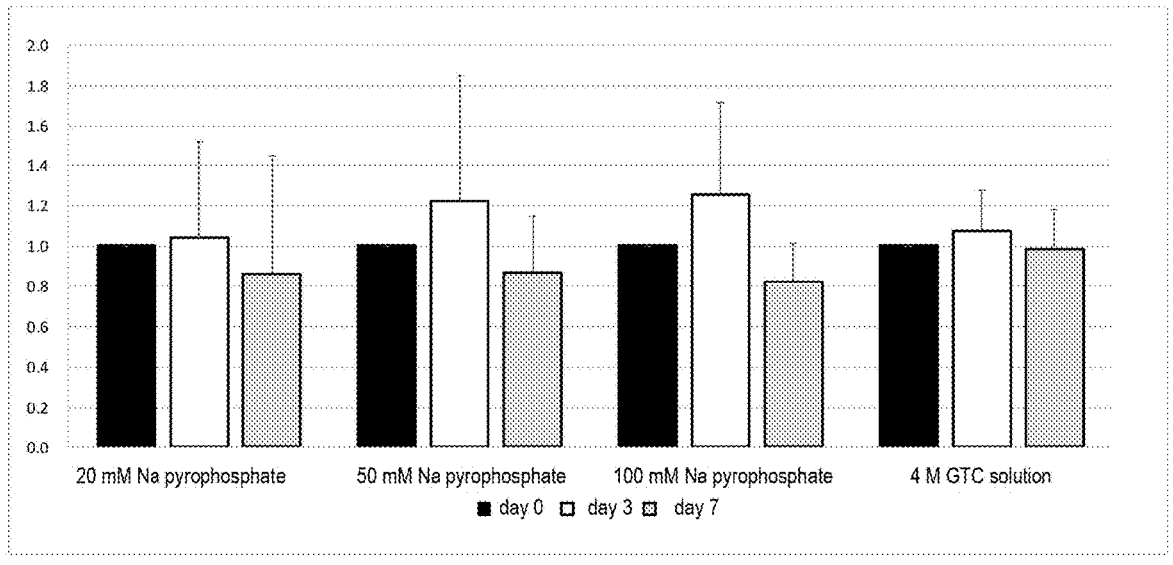
FIG. 19 is a graph illustrating results of real time PCR performed on DNAs extracted from each sample suspension before storage of a feces sample in each sample preservation solution (day 0) and after the storage for a prescribed period (day 3 and day 7) in Comparative Example 3.

In FIG. 19, the ordinate indicates the ratio obtained by using, as a reference (reference value of 1), the number of copies of the target gene obtained in the sample suspension (storage day 0). It was found based on the results that the number of copies of the target gene was largely increased/decreased as compared with that before the storage when the sample preservation solution singly containing sodium pyrophosphate was used. As the concentration of sodium pyrophosphate blended was higher, the degree of the change of the ratio tended to be larger, and hence it was presumed that sodium pyrophosphate may possibly accelerate the growth and action of microbes contained in a feces sample. Example 7 reveals, however, that a sample preservation solution capable of stably preserving a DNA of microbes even under a condition of 30° C. can be obtained by combining sodium pyrophosphate with the "4 M GTC solution" containing 4 M guanidinium thiocyanate, 100 mM Tris-HCl and 40 mM EDTA (pH 8.0).

It is noted that the present invention is not limited to the above-described embodiments and examples, and the technical scope of the present invention embraces various design changes and modifications made within the scope of the present invention defined by the appended claims.

REFERENCE SIGNS LIST

1, 10 analysis device
2, 20 cover member
3 preservation container
4 sample collecting member
41 axial portion
42 collecting portion
43 hole
5 pressing member
5a pressing pin
S sample preservation solution
C sample

SEQUENCE LISTING FREE TEXT

SEQ ID NO: 1: forward primer for PCR amplification of 16S rRNA gene region
SEQ ID NO: 2: reverse primer for PCR amplification of 16S rRNA gene region

The invention claimed is:

1. A sample preservation solution used for analyzing at least one component selected from the group consisting of bile acids, phenols, indoles and organic acids contained in a biological or environmental sample, comprising both (A) and (B):

(A) condensed phosphate; and (B) guanidinium thiocyanate, Tris-HCl (pH 7 to 9), and EDTA.

2. The sample preservation solution according to claim 1, wherein the condensed phosphate is 5 mM to 150 mM sodium pyrophosphate.

3. The sample preservation solution according to claim 1, wherein a concentration of the guanidinium thiocyanate is 0.1 M to 5 M, a concentration of the Tris-HCl (pH 7 to 9) is 40 mM to 150 mM, and a concentration of the EDTA is 1 mM to 50 mM.

4. The sample preservation solution according to claim 1, wherein the sample is feces.

* * * * *

SEQUENCE LISTING

```
<160> NUMBER OF SEQ ID NOS: 2

<210> SEQ ID NO 1
<211> LENGTH: 17
<212> TYPE: DNA
<213> ORGANISM: Artificial Sequence
<220> FEATURE:
<223> OTHER INFORMATION: forward primer

<400> SEQUENCE: 1
cctacgggag gcagcag                                              17

<210> SEQ ID NO 2
<211> LENGTH: 17
<212> TYPE: DNA
<213> ORGANISM: Artificial Sequence
<220> FEATURE:
<223> OTHER INFORMATION: reverse primer

<400> SEQUENCE: 2
attaccgcgg ctgctgg                                              17
```